United States Patent [19]
Breitman et al.

[11] Patent Number: 5,466,596
[45] Date of Patent: Nov. 14, 1995

[54] TISSUE SPECIFIC TRANSCRIPTIONAL REGULATORY ELEMENT

[75] Inventors: Martin L. Breitman, Willowdale; Daniel Dumont, Oakville; Gerard G. Gradwohl, Toronto, all of Canada

[73] Assignee: Mount Sinai Hospital Corporation, Toronto, Canada

[21] Appl. No.: 934,393

[22] Filed: Aug. 25, 1992

[51] Int. Cl.$^6$ .............................. C12N 5/10; C12N 15/11
[52] U.S. Cl. .................. 435/240.2; 435/69.1; 435/70.3; 536/24.1
[58] Field of Search ..................... 536/24.1; 435/69.1, 435/320.1, 70.3, 240.2

[56] References Cited

PUBLICATIONS

Dumont et al., Oncogene, 8:1293–1301, 1993.
Dumont et al., Oncogene, 7:1471–1480, 1992.
Dumont et al., J. of Cell. Biochem., vol. SUP O, No. 16 F, Apr. 3, 1992, p. 86, and Abstract from Keystone Symposium on Growth and Differentiation Factors in Vertebrate Development, Apr. 3, 1992, Abstract W204.
Yee, S. P. et al. (1989) P.N.A.S., U.S.A. 86, 5873–5877.
R. Jaenisch, PNAS U.S.A. 73, p. 1260 (1976).
R. Jaenisch, Cell 12, p. 691 (1977).
Old R. W. & Primrose, S. B., Principles of Gene Manipulation An Introduction to Genetic Engineering, 4th ed. Oxford University, Press at pp. 63–66.
H. Varmus, in RNA Tumor Viruses, R. Weiss et al., Cold Spring Harbor, N.Y., (1982) pp. 369–512.
D. Jahner and R. Jaenisch, Nature 287, p. 456 (1980).
R. Jaenisch et al., Cell 24, p. 519 (1981).
Lavitrano, M., et al., Cell. 57, p. 717 (1989).
A. Bradley et al., Nature 309, p. 255 (1984).
A. Gossler et al., PNAS U.S.A. 83, p. 9065 (1986).
Malone T. E. and R. J. Sharpe, TIPS, Nov. 1990 vol. 11 p. 457.
Nabel et al., JACC vol. 17, No. 6, p. 189B, 1991.
Matthews, W. et al., Proc. Natl. Acad. Sci. U.S.A., 88:9026–9030, 1991.

*Primary Examiner*—Richard A. Schwartz
*Assistant Examiner*—Nancy T. Vogel
*Attorney, Agent, or Firm*—Bereskin & Parr

[57] ABSTRACT

A novel transcriptional regulatory element which is capable of directing expression of a gene specifically in cells of the endothelial lineage. The transcriptional regulatory element may be used to target expression of a gene in cells of the endothelial lineage.

10 Claims, 15 Drawing Sheets

```
   1 ATCAAGTTTCAAGACGTGATCGGAGAGGGCAACTTTGGCCAGGTTCTGAAGGCACGCATCAAGAAGGATG    70
      I  K  F  Q  D  V  I  G  E  G  N  F  G  Q  V  L  K  A  R  I  K  K  D  G
  71 GGTTACGGATGGATGCCGCCATCAAGAGGATGAAAGAGTATGCCTCCAAAGATGATCACAGGGACTTCGC   140
      L  R  M  D  A  A  I  K  R  M  K  E  Y  A  S  K  D  D  H  R  D  F  A
 141 AGGAGAACTGGAGGTTCTTTGTAAACTTGGACACCATCCAAACATCATTAATCTCTTGGGAGCATGTGAA   210
      G  E  L  E  V  L  C  K  L  G  H  H  P  N  I  I  N  L  L  G  A  C  E
 211 CACCGAGGCTATTTGTACCTAGCTATTGAGTATGCCCCGCATGGAAACCTCCTGGACTTCCTGCGTAAGA   280
      H  R  G  Y  L  Y  L  A  I  E  Y  A  P  H  G  N  L  L  D  F  L  R  K  S
 281 GCAGAGTGCTAGAGACAGACCCTGCTTTTGCCATCGCCAACAGTACAGCTTCCACACTGTCCTCCCAACA   350
      R  V  L  E  T  D  P  A  F  A  I  A  N  S  T  A  S  T  L  S  S  Q  Q
 351 GCTTCTTCATTTTGCTGCAGATGTGGCCCGGGGGATGGACTACTTGAGCCAGAAACAGTTTATCCACAGG   420
      L  L  H  F  A  A  D  V  A  R  G  M  D  Y  L  S  Q  K  Q  F  I  H  R
 421 GACCTGGCTGCCAGAAACATTTTAGTTGGTGAAAACTACATAGCCAAAATAGCAGATTTTGGATTGTCAC   490
      D  L  A  A  R  N  I  L  V  G  E  N  Y  I  A  K  I  A  D  F  G  L  S  R
 491 GAGGTCAAGAAGTGTATGTGAAAAAGACAATGGGAAGGCTCCCAGTGCGTTGGATGGCAATCGAATCACT   560
      G  Q  E  V  Y  V  K  K  T  M  G  R  L  P  V  R  W  M  A  I  E  S  L
 561 GAACTATAGTGTCTATACAACCAACAGTGATGTCTGGTCCTATGGTGTATTGCTCTGGGAGATTGTTAGC   630
      N  Y  S  V  Y  T  T  N  S  D  V  W  S  Y  G  V  L  L  W  E  I  V  S
 631 TTAGGAGGCACCCCCTACTGCGGCATGACGTGCGCGGAGCTCTATGAGAAGCTACCCCAGGGCTACAGGC   700
      L  G  G  T  P  Y  C  G  M  T  C  A  E  L  Y  E  K  L  P  Q  G  Y  R  L
 701 TGGAGAAGCCCCTGAACTGTGATGATGAGGTGTATGATCTAATGAGACAGTGCTGGAGGGAGAAGCCTTA   770
      E  K  P  L  N  C  D  D  E  V  Y  D  L  M  R  Q  C  W  R  E  K  P  Y
 771 TGAGAGACCATCATTTGCCCAGATATTGGTGTCCTTAAACAGGATGCTGGAAGAACGGAAGACATACGTG   840
      E  R  P  S  F  A  Q  I  L  V  S  L  N  R  M  L  E  E  R  K  T  Y  V
 841 AACACCACACTGTATGAGAAGTTTACCTATGCAGGAATTGACTGCTCTGCGGAAGAAGCAGCCTAGAGCA   910
      N  T  T  L  Y  E  K  F  T  Y  A  G  I  D  C  S  A  E  E  A  A  *
 911 GAACTCTTCATGTACAACGGCCATTTCTCCTCACTGGCGCGAGAGCCTTGACACCTGTACCAAGCAAGCC   980
 981 ACCCACTGCCAAGAGATGTGATATATAAGTGTATATATTGTGCTGTGTTTGGGACCCTCCTCATACAGCT  1050
1051 CGTGCGGATCTGCAGTGTGTTCTGACTCTAATGTGACTGTATATACTGCTCGGAGTAAGAATGTGCTAAG  1120
1121 ATCAGAATGCCTGTTCGTGGTTTCATATAATATATTTTTCTAAAAGCATAGATTGCACAGGAAGGTATGA  1190
1191 GTACAAATACTGTAATGCATAACTTGTTATTGTCCTAGATGTGTTTGACATTTTTCCTTTACAACTGAAT  1260
1261 GCTATAAAAGTGTTTTGCTGTGTGCGCGTAAGATACTGTTCGTTAAAATAAGCATTCCCTTGACAGCACA  1330
1331 GGAAGAAAAGCGAGGGAAATGTATGGATTATATTAAATGTGGGTTACTACACAAGAGGCCGAACATTCCA  1400
1401 AGTAGCAGAAGAGAGGGTCTCTCAACTCTGCTCCTCACCTGCAGAAGCCAGTTTGTTTGGCCATGTGACA  1470
1471 ATTGTCCTGTGTTTTTATAGCACCCAAATCATTCTAAAATATGAACATCTAAAAACTTTGCTAGGAGACT  1540
1541 AAGAACCTTTGGAGAGATAGATATAAGTACGGTCAAAAAACAAAACTGCGCCATGGTACCC  1601
``` tek promoter studies

FIGURE 11

```
KpnI//   1  GCAAGTGCTG  CTCCCCGTGC  CCCAAAGCCC  CTTCTGTCAG  GGATCCCAAA
        51  TGCACCCCAG  AGAACAGCTT  AGCCTGCAAG  GGCTGGTCCT  CATCGCATAC
       101  CATACATAGT  GGAGGCTTGT  TATTCAATTC  CTGGCCTATG  AGAGGATACC
       151  CCTATTGTTC  CTGAAAATGC  TGACCAGGAC  CTTACTTGTA  ACAAAGATCC
       201  CTCTGCCCCA  CAATCCAGTT  AAGGCAGGAG  CAGGACCGGA  GCAGGAGCAG
       251  AAGATAAGCC  TTGGATGAAG  GGCAAGATGG  ATAGGGCTCG  CTCTGCCCCA
       301  AGCCCTGCTG  ATACCAAGTG  CCTTTAAGAT  ACAGCCTTTC  CCATCCTAAT
       351  CTGCAAAGGA  AACAGGAAAA  AGGAACTTAA  CCCTCCCTGT  GCTCAGACAG
                                                              ⌐ Exon I
       401  AAATGAGACT  GTTACCGCCT  GCTTCTGTGG  TGTTTCTCCT  TGCC[GCCAAC
       451  TTGTAAACAA  GAGCGAGTGG  ACCATGAGAG  CGGGAAGTCG  CAAAGTTGTG
       501  AGTTGTTGAA  AGCTTCCCAG  GGACTCATGC  TCATCTGTGG  ACGCTGGATG
                           Met (Start of translation)
       551  GGGAGATCTG  GGGAAGTATG  GACTCTTTAG  CCGGCTTAGT  TCTCTGTGGA
            *|Bgl II|
                                  ⌐ Intron I
       601  GTCAGCTTGC  TCCTTTATG]G  TAAGTTTTGG  CTTGATGTTT  ATTTGTGTGT
       651  GTGTGTCATG  TTTTAACAAC  AGTGACTTCT  CGCCATTCTC  TCTCTCACCA
       701  AACCTTCGAT  TTGGTGACCC  TGACACTGCT  TTTCTGAGAC  TCTCCAGTTT
       751  ACACATGGCA  ACGGTTTTGA  AGTTCAGATT  CCAGCGGCAC  CAGCTGGTTT
       801  TCAGCCATCT  TCTTGTAGAC  AGATGCTGCC  TTCCTGGGTT  GCCACGG
```

* The nucleotide fragment from this Bgl II restriction site to the Kpn I site was used to create the lac Z reporter construct. The Bgl II site is +9 nucleotides from the start of transcription.

```
Tek                                                  IKFQDVIGEGNFGQVLKAR---IKKD GLR--MDAAIKRMKEYASKD DHRDFAGELEVLCKLG MHPMIINLLGACEHR GYLYLAIEYAPHG        85
Jtk14
Ret                                                  LVLGKTL...E..K.V..TAFHL.GR AGY--TTV.V.ML..M..PS EL..LLS.FN...-QV N..HV.K.Y...SQD .P.L.IK...KY.       543
FlgM                                                 LVLGKPL....C....VL.EAIGLD.. KPNRVTKV.V.ML.SD.TEK .LS.LIS.M.MWKMI. K.K........TQD .P..VIV...SK.       567
                                                                          I                                 II                       III                    IV                       V

Tek            MLLDFL RKSRVLETDPAFAIAMSTAST------ LSSQQLLMFAADVARGMDYLSQKOFIHRDLAARNILVGENY IAKIADFGLSR---GQEV                                             169
Jtk14                                                                     V.....L AS...........E..                                                         32
Ret            S.RG.. .E..KVGPGYLGSGGSRNS.SLOMPDERA .TMGD.IS..MQISQ..Q..AEMKLV..........A.GR WM..S......DVYEEDP                                             638
FlgM           ..REY. QAR.PPGLEYCYMPSHMPEEQ------- ...KD.VSC.YQ.....E..AS.KC......V..T.DN VM......A.DIHHIDY                                                664
                      Insert                                                                               VI                        VII Tek            YVKK THGRLPVRMHAIESL NYSVYTT-MSDVWSYGVLLMEIVSLGGTPYCG MTCADVYEKLPQGYRLEKPLN CDDEVYHVMRQCWREKPYER                                           260
Jtk14          .... ..............K......F.                                                                                                                65
Ret            ...R SQ..I..K...... FDHI....Q.....F......T...M..P. IPPERLFML.KT.H.M.R.D. .SE.M.R..L...KQE.DK.                                              729
FlgM           .K.T .M....K...P.A. FDRI..-HQ.....F......FT...S..P. VPVEELFKL.KE.H.MD..S. .TM.L.MM..D..MAV.SQ.                                              745
                            VIII                              IX                             X                           XI Tek            PSFAQILVSL -NRML-EERKTVWNTLYEKFTYAGI-DC-SAEEAA 301
Jtk14
Ret            .V..D.SKD. E.M.VK-..RD.LDLAASTPSDSLIYD.GL.E..TP 772
FlgM           .T.K.LVED. DHIV..TSMQE.LDLSIPLDQYSPSFP.TR.STCSS 790
```

TISSUE SPECIFIC TRANSCRIPTIONAL REGULATORY ELEMENT

FIELD OF THE INVENTION

The invention relates to a novel transcriptional regulatory element which is capable of directing expression of a gene specifically in cells of the endothelial lineage; a recombinant molecule containing the transcriptional regulatory element; a transformant host cell including the recombinant molecule; a DNA construct comprising the transcriptional regulatory element operatively linked to a gene and a reporter gene; and, the use of the transcriptional regulatory element to target expression of a gene in cells of the endothelial lineage.

BACKGROUND OF THE INVENTION

Tissue specific transcriptional regulatory elements have been identified which have been used to target expression of exogenous genes in cells and in transgenic animals. For example, DNA constructs using an erythroid specific transcriptional element and an oncogene encoding a protein having protein-tyrosine kinase (PTK) activity have been used to produce transgenic animals which have cardiovascular disease (Yee, S.P. et al. (1989) P.N.A.S., U.S.A. 86, 5873-5877).

The ability to introduce into animals exogenous genes which are selectively expressed in a particular cell type provides wide ranging experimental as well as practical opportunities. In particular it permits investigation of the role of a substance in the development, determination, migration, or proliferation of cells of a particular lineage.

SUMMARY OF THE INVENTION

The present inventors have identified a transcriptional regulatory element characterized by endothelial specific expression. The element is expressed in cells of the endothelial lineage including mature and progenitor cells. This is the first report of a transcriptional regulatory element which is capable of directing expression specifically in cells of the endothelial lineage.

The present invention therefore provides a transcriptional regulatory element which is capable of directing expression of a gene specifically in cells of the endothelial lineage. Preferably, the transcriptional regulatory element comprises the initiation codon and the untranslated sequences of tek, a protein tyrosine kinase expressed during murine cardiogenesis. Most preferably, the transcriptional regulatory element is a 7.2 kb fragment extending from the Bgl II site to the Kpn I site as shown in FIG. 3.

The invention further provides a method of preparing the transcriptional regulatory element. The transcriptional regulatory element may be constructed by synthesis and ligation of DNA oligomers. The element may also be isolated by selectively amplifying the region of the transcriptional regulatory element using the polymerase chain reaction method and genomic DNA.

The invention also permits the construction of nucleotide probes which are unique to the transcriptional regulatory element of the invention. Thus, the invention also relates to a probe comprising a nucleotide sequence substantially homologous to the transcriptional regulatory element of the invention. The probe may be labelled, for example, with a radioactive substance and it may be used to select from a mixture of nucleotide sequences a transcriptional regulatory element of the invention or an element homologous thereto.

The invention also relates to a recombinant molecule adapted for transformation of a host cell comprising a transcriptional regulatory element of the invention and a gene operatively linked to the transcriptional regulatory element. A transformant host cell including a recombinant molecule of the invention is also provided. Still further, this invention provides plasmids which comprise the transcriptional regulatory element of the invention.

In an embodiment of the invention a recombinant molecule comprising the transcriptional regulatory element of the invention operatively linked to a gene and a reporter gene is provided.

The recombinant molecules of the invention may be used to produce transgenic non-human mammals. Accordingly the invention relates to a method of producing a transgenic non-human mammal characterized as having a plurality of cells containing a recombinant molecule of the invention, or an ancestor of the mammal at an embryonic stage, comprising (a) introducing the recombinant molecule into a pronucleus of a mammalian zygote by microinjection, said zygote being capable of development into a mammal, thereby obtaining a genetically transformed zygote; (b) transplanting an embryo derived from the genetically transformed zygote into a pseudo-pregnant female capable of bearing the embryo to term and (c) if desired allowing the embryo to develop to term.

The invention further relates to a transgenic non-human mammal all of whose germ cells and somatic cells contain a recombinant molecule of the invention introduced into the mammal, or an ancestor of the mammal at an embryonic stage. Still further the invention relates to cell cultures of cells of the transgenic mammals.

The invention also relates to a method of determining the affect of a substance on cells of the endothelial lineage comprising producing a transgenic non-human mammal characterized as having a plurality of cells containing a recombinant molecule comprising the transcriptional regulatory element of the invention operatively linked to a gene encoding the substance, or an ancestor of the mammal at an embryonic stage, comprising (a) introducing the recombinant molecule into a pronucleus of a mammalian zygote by microinjection, said zygote being capable of development into a mammal, thereby obtaining a genetically transformed zygote; (b) transplanting an embryo derived from the genetically transformed zygote into a pseudo-pregnant female capable of bearing the embryo to term and (c) isolating the embryo or allowing the embryo to develop to term, and (d) determining the affect of the substance on cells of the endothelial lineage by comparison to a control.

In an embodiment of the invention, a method of determining the affect of a substance on cells of the endothelial lineage is provided comprising producing a transgenic non-human mammal characterized as having a plurality of cells containing a recombinant molecule comprising the transcriptional regulatory element of the invention operatively linked to a gene and a reporter gene encoding a phenotype which is not displayed by the mammal, or an ancestor of the mammal at an embryonic stage, comprising (a) introducing the recombinant molecule into a pronucleus of a mammalian zygote by microinjection, said zygote being capable of development into a mammal, thereby obtaining a genetically transformed zygote; (b) transplanting an embryo derived from the genetically transformed zygote into a pseudo-pregnant female capable of bearing the embryo to term and (c) isolating the embryo or allowing the embryo to develop to term, (d) assaying for the phenotype of the reporter gene in the embryo or transgenic non-human mammal to determine the pattern and extent of expression of the gene, and (e) determining the affect of the substance on cells of the endothelial lineage by

DESCRIPTION OF THE DRAWINGS

The invention will be better understood with reference to the drawings in which:

FIG. 1 (SEQ ID NO: 1) shows the nucleotide and deduced amino acid sequence of tek;

FIG. 2 (SEQ ID NO: 3) shows the nucleotide and deduced amino sequence of a 1601 bp DNA segment of tek;

FIG. 11 (SEQ ID NO: 5) shows the partial nucleotide sequence of the transcriptional regulatory element of the invention;

FIG. 14 shows a comparison of a portion of the deduced amino acid sequence of the novel receptor tyrosine kinase protein of the invention with that of other tyrosine kinases.

DETAILED DESCRIPTION OF THE INVENTION

Copending application Ser. No. 07/921,795 relates to a novel protein tyrosine kinase expressed during murine cardiogenesis which is designated tek. The tek locus was mapped to chromosome 4, between the brown and pmv-23 loci. This region is syntenic with human chromosomal regions 1p22-32, 9q31-33, and 9p22-13. The deduced amino acid sequence of tek predicts that it encodes a putative receptor tyrosine kinase that contains a 21 amino acid kinase insert and which is most closely related in its catalytic domain to FGFR1 (mouse fibroblast growth factor) and the product of the ret proto-oncogene. FIG. 1 (and SEQ ID NOS: 1 and 2 in the Sequence Listing); shows the nucleotide and deduced amino acid sequence of tek. The present inventors have also identified the initiation site of translation of tek.

In the adult and all stages of embryonic development examined, tek expression was found to be restricted to cells of the endothelial lineage. Specifically, in situ hybridization analysis of adult tissues, as well as sectioned and whole mount embryos, showed that tek is specifically expressed in the endocardium, the leptomeninges and the endothelial lining of the vasculature from the earliest stages of their development. Moreover, examination of the morphology of tek-expressing cells, and staging of tek expression relative to that of the endothelial cell marker von Willebrand factor, revealed that tek is expressed prior to von Willebrand factor and appears to mark the embryonic progenitors of mature endothelial cells.

The present inventors have identified a transcriptional regulatory element located upstream of tek which specifically directs expression of a gene in cells of the endothelial lineage. The transcriptional regulatory element has been found to direct expression in both mature and progenitor endothelial cells.

Figure 3:
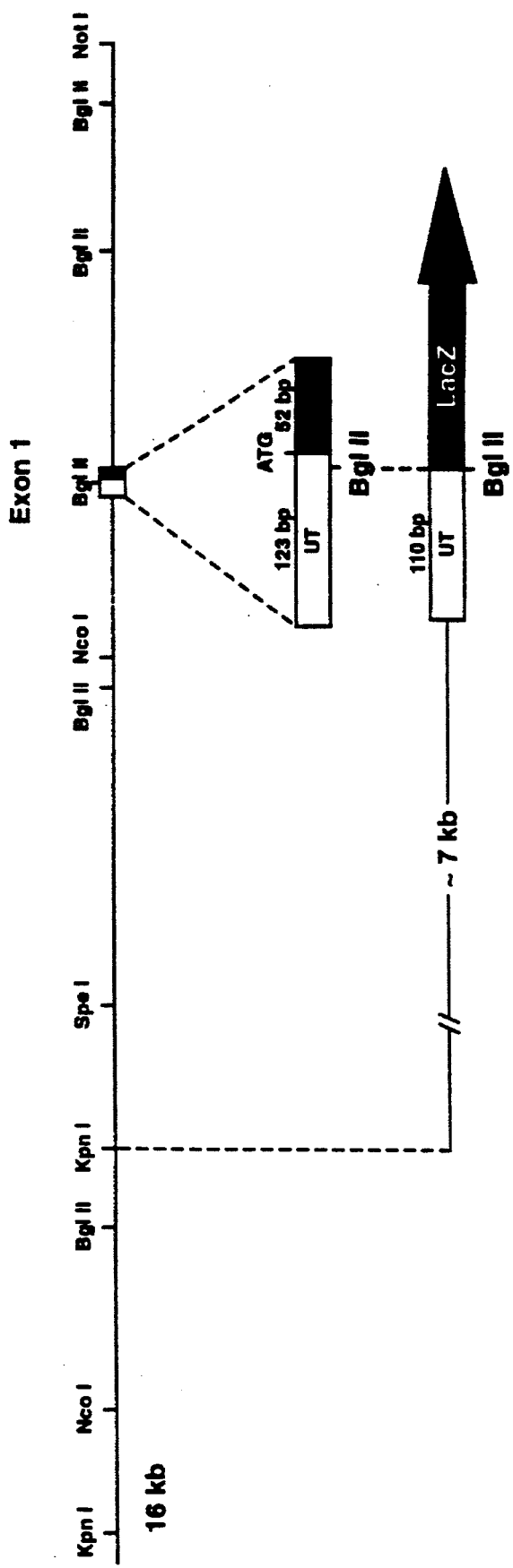
FIG. 3 is a restriction map showing the transcriptional regulatory element of the invention fused to reporter gene LacZ.
Figure 4:
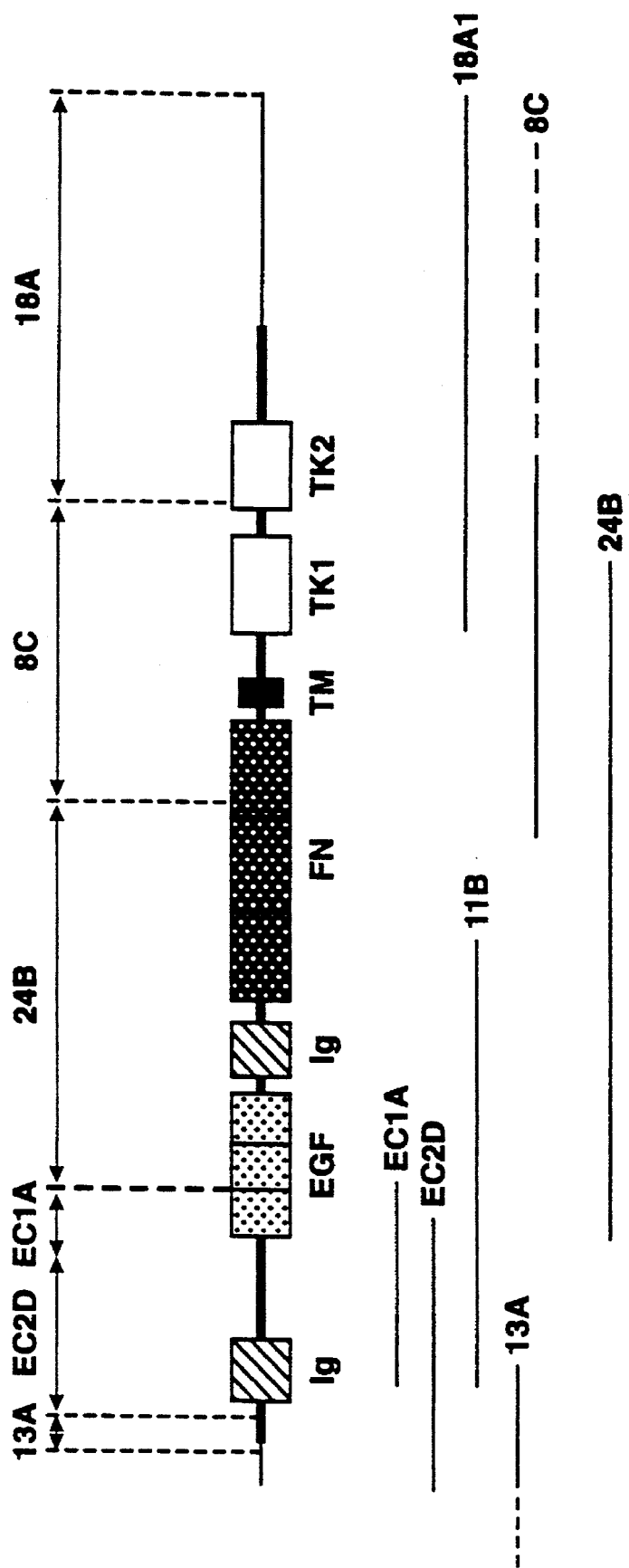
FIG. 4 is a schematic diagram showing the predicted structure of tek.

In particular, the present inventors isolated a DNA segment from a mouse genomic bacteriophage library using a 5'-prime probe which contained the initiation codon and untranslated sequences of tek using the procedures of Sambrook et al., 1989, Molecular Cloning, A Laboratory Manual. Cold Spring Harbour Lab. Press. A 16 kb phage clone was shown by hybridization and sequence analysis to contain a single exon with 175 bp homologous to the cDNA. A DNA fragment extending from the Bgl II restriction site located at nucleotide 110 of the cDNA to the nearest Kpn I in the phage was cloned upstream of the bacterial gene lacZ (see FIG. 3). This reporter construct containing 7.2 kb of the tek gene was microinjected into pronuclei of fertilized randomly bred CD-1 mice using procedures as set out in Hogan et al. (1986, Manipulating the Mouse Embryo, A Laboratory Manual. Cold Spring Harbor Lab. Press). Three transgenic founder embryos were dissected from their foster mothers and yolk sac DNA analyzed for the presence of the transgene. Expression of the transgene was determined by the X-gal staining of whole embryos and subsequent sectioning of the embryos. The 7.2 kb fragment was able to drive lacZ expression in endothelial cells that had previously been shown to express tek RNA thus demonstrating that this DNA contained the tek transcriptional regulatory element. The partial nucleotide sequence of the transcriptional regulatory element is shown in FIG. 11 and in the Sequence Listing as SEQ ID NO: 5.

The invention further provides a method of preparing the transcriptional regulatory element. The transcriptional regulatory element may be isolated by selectively amplifying the region of the transcriptional regulatory element using the polymerase chain reaction method and genomic DNA. It is possible to design synthetic oligonucleotide primers from the sequence shown in FIG. 11 for use in PCR and for screening genomic libraries. An amplified fragment can be cloned and characterized by DNA sequence analysis. The nucleotide sequence of the transcriptional regulatory element will also permit the element to be constructed by synthesis and ligation of DNA oligomers. The transcriptional regulatory element may be proven functional by assessing the transient expression of a construct bearing a reporter gene. For example, using the reporter gene for B-galactosidase (LacZ) or chloramphenicol acetyltransferase (CAT) after transfection of the DNA into host cells.

It will be appreciated that the invention includes nucleotide sequences which have substantial sequence homology with the nucleotide sequence of the transcriptional regulatory element of the invention. The term "sequences having substantial sequence homology" means those sequences which have slight or inconsequential sequence variations i.e. the homologous sequences function in substantially the same manner to produce substantially the same result as the actual sequence. The variations may be attributable to local mutations or structural modifications.

The invention also permits the construction of nucleotide probes which are unique to the transcriptional regulatory element of the invention. Thus, the invention also relates to a probe comprising a nucleotide sequence substantially homologous to the transcriptional regulatory element of the invention. The probe may be labelled and it may be used to select from a mixture of nucleotide sequences a transcriptional regulatory element of the invention or an element substantially homologous thereto. A nucleotide probe may be labelled with a radioactive label which provides for an adequate signal and has sufficient half-life such as $^{32}P$, $^{3}H$, $^{14}C$ or the like. Other labels which may be used include antigens that are recognized by a specific labelled antibody, fluorescent compounds, enzymes, antibodies specific for a labelled antigen, and chemiluminescent substances. An appropriate label may be selected having regard to the rate of hybridization and binding of the probe to the nucleotide to be detected and the amount of nucleotide available for hybridization.

The invention also relates to a recombinant molecule adapted for transformation of a host cell comprising a transcriptional regulatory element of the invention and a gene operatively linked thereto. The transcriptional regulatory element of the invention operatively linked to a gene may be incorporated in a known manner into a recombinant molecule which ensures good expression of the protein encoded by the gene. The transcriptional regulatory element of the invention may be incorporated into a plasmid vector, for example, a retroviral vector, pECE.

The transcriptional regulatory element of the invention may be operatively linked to a reporter gene or a gene encoding a substance which has toxic or therapeutic activity including a factor which modulates angiogenesis. Examples of reporter genes, factors which modulate angiogenesis, and substances with toxic or therapeutic activity are discussed below.

A transformant host cell including a recombinant molecule of the invention and a cell line containing such transformant host cells is also provided. Examples of suitable host cells include human endothelial cells such as umbilical vein endothelial cells and rabbit aortic endothelial cells.

The invention also relates to a recombinant molecule comprising a transcriptional regulatory element of the invention operatively linked to a gene and a reporter gene. The reporter gene may be introduced into the recombinant molecule using conventional methods such as those described in Sambrook et al., 1989, Molecular Cloning, A Laboratory Manual. Cold Spring Harbour Lab. Press. The recombinant molecule may also be synthetically produced using conventional methods. Further, the recombinant molecule may be introduced into a host cell using conventional methods.

The reporter gene should be under the control of the transcriptional regulatory element and the pattern and extent of expression of the gene operatively linked to the transcriptional regulatory element may accordingly be determined in cells of the endothelial lineage. Preferably the reporter gene codes for a phenotype not displayed by the host cell and the phenotype may be assayed quantitatively. Examples of suitable reporter genes include lacZ (B-galactosidase), neo (neomycin phosphotransferase), cat (chloramphenicol acetyltransferase) dhfr (dihydrofolate reductase), aphIV (hygromycin phosphotransferase), lux (luciferase), uidA (B-glucuronidase). Preferably, the reporter gene is lacZ which codes for B-galactosidase. B-galactosidase may be assayed using the lactose analogue X-gal(5-bromo-4-chloro3-indolyl-b-D-galactopyranoside) which is broken down by B-galactosidase to a product that is blue in color. (See for example Old R.W. & Primrose S.B., Principles of Gene Manipulation An Introduction to Genetic Engineering, 4th ed. Oxford University Press at pages 63–66 for a discussion of procedures for screening for recombinants).

The recombinant DNA of the invention may be used to produce transgenic non-human mammals. Accordingly the invention relates to a method of producing a transgenic non-human mammal characterized as having a plurality of cells containing a recombinant molecule of the invention, or an ancestor of the mammal at an embryonic stage, comprising (a) introducing the recombinant molecule into a pronucleus of a mammalian zygote by microinjection, said zygote being capable of development into a mammal, thereby obtaining a genetically transformed zygote; (b) transplanting an embryo derived from the genetically transformed zygote into a pseudo-pregnant female capable of bearing the embryo to term and (c) if desired, allowing the embryo to develop to term.

The invention further relates to a transgenic non-human mammal all of whose germ cells and somatic cells contain a recombinant molecule of the invention introduced into the animal, or an ancestor of the mammal at an embryonic stage.

In a preferred embodiment, plasmids containing recombinant molecules of the invention (for example see FIG. 3) are microinjected into mouse embryos. In particular, the plasmids are injected into the male pronuclei of fertilized one-cell mouse eggs; the injected eggs are transferred to pseudo-pregnant foster females; and, the eggs in the foster females are allowed to develop to term. (Hogan, B. et al, (1986) A Laboratory Manual, Cold Spring Harbor, N.Y., Cold Spring Harbor Laboratory).

It will be realized that methods other than microinjection can be used to generate the transgenic mammals. For instance, retrovirus infection techniques (R. Jaenisch, PNAS U.S.A. 73, p. 1260 (1976); Cell 12, p. 691 (1977); H. Varmus, in RNA Tumor Viruses, R. Weiss et al, Cold Spring Harbor Laboratory, Cold Spring Harbor, N.Y., (1982) p. 369–512; D. Jahner and R. Scienisch, Nature 287, p. 456 (1980) and R. Jaenisch et al, Cell 24, p. 519 (1981)), direct introduction of DNA into sperm cells followed by in vitro fertilization (Lavitrano, M., et al, Cell. 57, p. 717), and techniques involving the introduction of DNA by viral transduction or transfection into embryonic stem cells which are able to contribute to the germ line when injected into host blastocysts can be employed (A. Bradley et al, Nature 309, p. 255 (1984); A. Gossler et al, PNAS U.S.A. 83, p. 9065 (1986)).

Although experimental animals used in the preferred embodiment disclosed were mice, the invention should not be limited thereto. It may be desirable to use other species such as rats, hamsters and rabbits.

The invention also relates to a method of determining the affect of a substance on cells of the endothelial lineage comprising producing a transgenic non-human mammal characterized as having a plurality of cells containing a recombinant molecule comprising the transcriptional regulatory element of the invention operatively linked to a gene, or an ancestor of the mammal at an embryonic stage, comprising (a) introducing the recombinant molecule into a pronucleus of a mammalian zygote by microinjection, said zygote being capable of development into a mammal, thereby obtaining a genetically transformed zygote; (b) transplanting an embryo derived from the genetically transformed zygote into a pseudo-pregnant female capable of bearing the embryo to term and (c) isolating the embryo or allowing the embryo to develop to term, and (d) determining the affect of the substance on cells of the endothelial lineage by comparison to a control.

In an embodiment of the invention a method of determining the affect of a substance on cells of the endothelial lineage is provided comprising producing a transgenic non-human mammal characterized as having a plurality of cells containing a recombinant molecule comprising a transcriptional regulatory element of the invention linked to a gene encoding the substance, and a reporter gene encoding a phenotype which is not displayed by the mammal, or an ancestor of the mammal at an embryonic stage, comprising (a) introducing the recombinant molecule into a pronucleus of a mammalian zygote by microinjection, said zygote being capable of development into a mammal, thereby obtaining a genetically transformed zygote; (b) transplanting an embryo derived from the genetically transformed zygote into a pseudo-pregnant female capable of bearing the embryo to term and (c) if desired, allowing the embryo to develop to term, (d) assaying for the phenotype of the reporter gene in the embryo or transgenic mammal to determine the pattern and extent of expression of the gene, and (e) determining the affect of the substance on cells of the endothelial lineage by comparison to a standard.

As discussed above, the reporter gene should be under the control of the transcriptional regulatory element and accordingly the pattern and extent of expression of a gene operatively linked to the transcriptional regulatory element may be determined by assaying for the phenotype of the reporter gene. Preferably the reporter gene codes for a phenotype not displayed by the host cell and the phenotype may be assayed quantitatively. Examples of suitable reporter genes include lacZ (β-galactosidase), neo (neomycin phophotransferase), cat (chloramphenicol acetyltransferase) dhfr (dihydrofolate reductase), aphIV (hygromycin phosphotransferase), lux (luciferase), uidA (β-glucuronidase). Preferably, the reporter gene is lacZ which codes for β-galactosidase. β-galactosidase may be assayed using the lactose analogue X-gal(5-gromo-4-chloro-3-indolyl-β-D-galactopyranoside) which is broken down by β-galactosidase to a product that is blue in color. (See for example Old R. W. & Primrose S. B., Principles of Gene Manipulation An Introduction to Genetic Engineering, 4th ed. Oxford University Press at pages 63–66 for a discussion of procedures for screening for recombinants).

Cells of the transgenic mammals of the invention and produced by the methods of the invention may be cultured using standard tissue culture techniques.

The present invention allows the manipulation of endothelial cell physiology by targeting expression of a substance in cells of the endothelial lineage in a mammal. The above described methods, transgenic animals and cell cultures derived therefrom, can therefore be used to assess the role of a substance in the determination, migration, or proliferation of cells of the endothelial lineage. In particular, the invention provides a mechanism for investigating vascularization of tumors and the control of angiogenesis. A transgenic mammal may be produced which expresses a substance exclusively in cells of the endothelial lineage. A comparison of endothelial phenotype, morphology, and function using for example immunohistochemical techniques and assays for LDL receptors, and of the pattern and extent of expression of the substance in the animal with a control transgenic animal will provide an indication of the affect of the substance on cells of the endothelial lineage.

Substance which may modulate the angiogenic process (herein also referred to as angiogenic factors) may be tested using the above described method. Examples of such substances include substances derived from human and animal tissues which stimulate the proliferation or migration of normally quiescent endothelial cells in culture or promote neovascularization in vivo including factors which are associated with the vascularization that permits tumor growth; substances which are inhibitors of angiogenesis such as transforming growth factor β, tumor necrosis factor α, human platelet factor 4 (PF4) and α interferon; substances which suppress cell migration, such as proteinase inhibitors which inhibit proteases which may be necessary for penetration of the basement membrane, in particular, tissue inhibitors of metalloproteinase TIMP-1 and TIMP-2; and other proteins such as protamine which has demonstrated angiostatic properties. For a review of factors which play a role in angiogenesis see Maione T. E. and R. J. Sharpe, TIPS, November 1990 Vol. 11 page 457.

The transcriptional regulatory element of the invention may be used in gene therapy to introduce a foreign gene into endothelial cells to correct or prevent vascular disorders. (See Nabel et al., JACC Vol 17, No. 6, page 189B, 1991 for a discussion of gene transfer into vascular cells). For example, the transcriptional regulatory element of the invention may be used to express foreign genes at specific sites in the circulation. Endothelial cells are found at diseased sites and accordingly, the transcriptional regulatory element of the invention may be used to target therapeutic agents including anticoagulants, vasodilator, and angiogenic factors (see above discussion) to endothelial cells found at diseased sites. Thus, genetic modification of endothelial cells utilizing the transcriptional regulatory element of the invention may be used in the treatment of acquired vascular disorders such as hypertension, atherosclerosis restenosis, arthritis and cancer.

Endothelial cells line all blood vessels and accordingly the transcriptional regulatory element of the invention may be used to target therapeutic agents into the bloodstream. Thus, genetic modification of endothelial cells utilizing the transcriptional regulatory element of the invention may also be used in the treatment of systemic or inherited disorders. For example, the transcriptional regulatory element of the invention could be operatively linked to the factor VIII gene and introduced into a population of endothelial cells to correct a hemophilia disorder.

Endothelial cells genetically modified in vitro using the transcriptional regulatory element of the invention i.e transformant host cells or cell lines containing transformant host cells of the invention, may be used to deliver gene products to the vasculature. In particular, endothelial cells genetically modified in vitro using the transcriptional regulatory element of the invention may be introduced into the vascular wall by catheterization. Using this method, therapeutic proteins may be introduced into diseased arterial segments. The method may be particularly useful for introducing growth inhibitor proteins into an angioplasty site in patients with restenosis who have undergone coronary angioplasty.

Endothelial cells genetically modified in vitro using the transcriptional regulatory element of the invention may be used to improve the performance of prosthetic vascular grafts. Prosthetic vascular grafts may be seeded with endothelial cells genetically modified using the transcriptional regulatory element of the invention, to produce therapeutic proteins which may prevent thrombosis or promote repopulation. Vascular stents may also be populated with genetically modified endothelial cells to reduce problems such as thrombosis.

A gene under the control of the transcriptional regulatory element of the invention i.e recombinant molecules of the invention, may be directly introduced into endothelial cells in vivo using delivery vehicles such as retroviral vectors, adenoviral vectors and DNA virus vectors. They may also be introduced into endothelial cells in vivo using physical techniques such as microinjection and electroporation or chemical methods such as coprecipitation and incorporation of DNA into liposomes.

The invention will be more fully understood by reference to the following examples. However, these examples are merely intended to illustrate embodiments of the invention and are not to be construed to limit the scope of the invention.

EXAMPLES

The following materials and methods were utilized in the investigations outlined in the examples:

DNAs

AKR/J, DBA, and AKR/J×DBA recombinant inbred mouse DNAs were obtained from Jackson Labs (Bar Harbor, Me.), digested with AccI, blotted to ZETA-probe nylon membrane (Bio-Rad), and probed with the 1.6 kb tek cDNA labelled by random priming (Feinberg, A. P. & Vogelstein, B. (1983) *Analyt. Biochem.*, 132, 6–13). Hybridization was performed overnight at 65° in 200 mM sodium phosphate pH7.0, 7% sodium dodecyl sulfate (SDS), 1% bovine serum albumin (BSA), and 1 mM EDTA. Filters were washed twice at 55° in 2×SSC (1×SSC=0.15M NaCl, 0.015M sodium citrate pH7.0) and 0.1% SDS and twice in 0.2×SSC and 0.1% SDS, and exposed overnight to Kodak XAR-5 film.

Mice

Embryos and adult mouse tissues were obtained from random bred CD-1 stocks (Charles River, Quebec). Embryos were staged as Day 0.5 on the morning of a vaginal plug.

RNA-Purification and Analysis

Total RNA was extracted from pools of 30 to 40 Day 9.5 and 12.5 murine embryonic hearts with RNAZOL (CINNA/B10TECX Lab. Int.), with some added modifications. Briefly, tissues were washed with ice cold phosphate buffered saline (PBS) and homogenized in 2.5 ml of RNAzol. Chloroform (250 µl) was added and the tubes were mixed vigorously and then chilled on ice for 15 min. The suspension was centrifuged for 15 min at 4° after which the aqueous phase was collected and re-extracted twice more with phenol/chloroform/isoamyl alcohol (25:24:1; vol:vol:vol). The RNA was precipitated with an equal volume of isopropanol, collected by centrifugation, and the pellet resuspended in diethylpyrocarbonate (DEPC)treated 0.4M sodium acetate, pH5.2. The RNA were then precipitated with two volumes of 95% ethanol, washed with 70% and 95% ethanol, dried, and resuspended in DEPC treated 0.3M sodium acetate, pH5.2. The RNA concentration was determined and the RNA stored at −70° until use.

Poly A-containing RNA was purified from a pool of 100 to 150 Day 12.5 murine embryonic hearts with a Quick-PREP mRNA isolation kit (Pharmacia) as outlined by the supplier.

For Northern blot hybridization, 5 µg of poly A-containing RNA from 12.5 day embryonic heart was electrophoresed through a formaldehyde-agarose gel and blotted to a ZETA-PROBE nylon membrane (Bio-Rad) according to established protocols (Sambrook et al., 1989, Molecular Cloning. Cold Spring Harbor Laboratory Press). The membrane was hybridized with a [$^{32}$P]-labelled antisense riboprobe synthesized from the 1.6 kb tek cDNA in run off reactions with SP6 RNA polymerase (Promega).

Reverse Transcription Coupled to the Polymerase Chain Reaction (RT-PCR).

First strand cDNA was synthesized in a total reaction volume of 20 µl containing 20 µg of total RNA, 200 units of Mo-MLV-reverse transcriptase (BRL), either 1 µg of oligo-d(T)$_{18}$ (Day 12.5 RNA) (Boerhinger Mannheim) or 2 µg of random hexamer primers (Day 9.5 RNA) (Boerhinger Mannheim), 1×PCR buffer (Cetus), 2.5 mM MgCl$_2$, 1 mM of dNTPs (Pharmacia), 40 units of RNAsin (Promega), and 12.5 mM dithiothreitol. The RNA was heated to 65° C. for 10 min and cooled quickly on ice prior to addition to the reaction components. The reaction was allowed to proceed for 1 h at 37° and then terminated by heating for 5 min at 95°. For PCR, the reaction mixture was adjusted to a final volume of 100 µl containing 1×PCR buffer, 1.5 mM MgCl$_2$, 800 µM dNTPs, and 1 µg of each of the two degenerate tyrosine kinase oligonucleotide primers described by Wilks, A.F. (1989) *Proc. Natl. Acad. Sci.*, 86, 1603–1607. Amplification was performed with a Ericomp thermocycler using the following parameters: denaturation for 2 min at 94°, annealing for 2 min at 42°, and extension for 4 min at 63°. After 40 cycles, the reaction products were collected by ethanol precipitation and electrophoresed through at 2% low-melt agarose (Sea Plaque) gel. In most cases a band of approximately 200 bp was visible within a background smear of ethidium bromide staining. This band was excised and recovered by three cycles of freeze-thaw in 100 µl of water. 10 µl of this solution was then subjected to a second round of PCR under the same conditions described above.

Cloning and Sequencing of RT-PCR Products.

After the second round of amplification, 10 µl of the reaction mixture were analyzed on a gel for successful amplification. The remaining 90 µl were then ethanol precipitated, digested with EcoRI and BamHI, gel purified, and ligated to pGEM7Zf+(Promega) digested with the same enzymes. The ligation mixture was then transformed into MV1190 competent cells, individual amp$^r$ colonies picked, plasmid DNA prepared, and the cDNA inserts analyzed by single track dideoxynucleotide sequencing (Sanger, F., Nicklen, S. & Coulson, A. R. (1977). *Proc. Natl. Acad. Sci.*, 74, 5463–5467). A single representative clone of each multiple isolate was sequenced in its entirety. Of the 58 clones analyzed, roughly 10% showed no sequence identity to tyrosine kinases and were disregarded.

Isolation of Additional tek cDNA Sequences.

Approximately $10^6$ plaques from an amplified, random primed 13.5 day murine embryonic λgt10 cDNA library were hybridized with the 210 bp tek PCR product labelled with [$^{32}$p]-dCTP by PCR. Hybridization was carried out overnight at 55° in 50% formamide, 10% dextran sulfate (Pharmacia), 0.5% BLOTTO, 4×SSPE (1×SSPE=0.18M NaCl, 10 mM $NaH_2PO_4$, 1 mM EDTA, pH7.4), 100 µg/ml sheared salmon sperm DNA, and $2\times10^6$ cpm/ml of probe. Filters were washed at 55° twice in 2×SSC containing 0.1% SDS and twice in 0.2×SSC containing 0.1% SDS, dried, and exposed overnight to Kodak XAR-5 film. One clone was isolated from this screen and was found to contain a 1.6 kb cDNA. The sequence of the 1.6 kb cDNA was determined by the method of Sanger et al. (1977) from a set of anchored deletions generated with a standardized kit (ERASE-A-BASE, Promega).

In Situ Hybridization

Embryos isolated on Day 12.5 were dissected away from all extraembryonic tissues whereas embryos at earlier time points were recovered in utero. Embryos and adult tissues were fixed overnight in 4% paraformaldehyde, dehydrated with alcohols and xylenes, and embedded in paraffin. Tissues were sectioned at 6 µm thickness and mounted on 3-aminopropyltriethoxysilane treated slides (Sigma). After removal of paraffin the samples were treated with predigested pronase (Boerhinger Mannheim), acetylated with triethanolamine, dehydrated, and hybridized according to the protocol described by Frohman, N. B., Boyle, M. & Martin, G. R. (1990), *Development*, 110, 589–607. Dark and bright field photomicroscopy was performed with a Leitz Vario Orthomat 2 photomicroscopic system. Adjacent sections probed with a tek sense probe produced no detectable signal above background.

Whole-mount in situ hybridizations were performed using a modification of existing procedures (Tautz, D. & Pfeifle, C. (1989). Chromosoma, 98, 81–85; Henmati-Brivanlou, A., Franck, D., Bolce, M. E., Brown, B. D., Sive, H. L. & Harland, R. M. (1990). *Development*, 110, 325–330; Conlon and Rossant, in prep.). The hybridization of single-stranded RNA probes labelled with digoxigenin was detected with antidigoxigenin antibodies coupled to alkaline phosphatase. The En2 cDNA was prepared as set forth in Joyner A. L. & Martin, G. R. (1987). *Genes and Dev.*, 1, 29–38 and expression of En2 is described in Davis, C. A., Holmyard, D. P., Millen, K. J. & Joyner, A. L. (1991) *Development*, 111:, 287–298.

Immunohistochemistry

Sections were stained immunohistochemically for von Willebrand factor with a commercially available kit (Biomeda). After color development, slides were counterstained with Harris hematoxylin.

EXAMPLE I

Isolation and Characterization of Tek

To identify and characterize tyrosine kinases expressed during murine cardiogenesis, cDNAs were synthesized from 9.5 and 12.5 day embryonic heart RNA by RT-PCR using degenerate oligonucleotide primers previously demonstrated to amplify tyrosine kinase sequences preferentially (Wilks, A. F. 1989, *Proc. Natl. Acad. Sci.*, 86, 1603–1607). Considerable cellular differentiation and morphogenesis have occurred within the cardiac region of the embryo by Day 9.5. At this stage the heart has developed from the primordial mesoderm cells of the cardiac plate into a primitive bent tube structure, consisting of two endothelial tubes enclosed within the developing myocardium. Between Day 9.5 and 12.5 the heart undergoes additional complex morphological changes in association with the formation of the four chambers and septa characteristic of the adult heart. Sequence analysis of 58 clones obtained following amplification revealed that whereas roughly 10% did not contain sequence similarities to protein kinases the remainder corresponded to 5 distinct cDNAs (Table 1-Identity and number of tyrosine kinase cDNA clones recovered from Day 9.5 and 12.5 murine embryonic heart by RT-PCR). Four of these cDNAs represented previously characterized tyrosine kinases including, bmk, c-src, c-abl, and the platelet derived growth factor receptor β-subunit (pdgfrb). The isolation of bmk, c-src, and c-abl is consistent with the broad tissue distribution of these kinases (Wang, J. Y. J. & Baltimore, D. (1983). *Mol. Cell. Biol.*, 3, 773–779; Ben-Neriah et al., (1986). *Cell*, 44, 577–586; Holtzman, D., Cook, W. & Dunn, A. (1987). *Proc. Natl. Acad. Sci.*, 84, 8325–8329; Renshaw, M. W., Capozza, M. A. & Wang, J. Y. J. (1988). *Mol. Cell. Biol.*, 8, 4547–4551). The recovery from embryonic heart of pdgfrb at a relatively high frequency may indicate that pdgfrb plays an important role in cardiogenesis, as has been suggested by recent studies demonstrating that the addition of PDGF-BB to explants of axolotol cardiac field mesoderm stimulates the production of beating bodies (Muslin, A. J. & Williams, L. T. (1991). *Development*, 112, 1095–1101) the fifth cDNA, which was also isolated at high frequency, was novel and for reasons that will become clear below was designated tek. The 210 bp RT-PCR-derived tek clone was subsequently used to isolate additional tek cDNA sequences.

FIG. 2 and SEQ ID NO:3 shows the nucleotide sequence of a 1.6 kb tek cDNA isolated from a 13.5 day mouse embryo cDNA library. Translation of this sequence reveals a single large open reading frame that terminates with TAG at nucleotide 907, followed by 696 nucleotides of 3' untranslated sequence. Several features of the deduced amino acid sequence suggest that the 1.6 kb tek cDNA encodes the cytoplasmic portion of a transmembrane RTK, consisting of the catalytic domain followed by a short carboxy-terminal tail of 33 amino acid residues.

FIG. 14 shows a comparison of the deduced amino acid sequence of tek with that of other tyrosine kinases; Identical sequences are denoted by periods. Dashes were added to allow for optimal alignment. The kinase insert and conserved regions of the catalytic domain are indicated beneath the aligned sequences (Hanks, S. K., Quinn, A. M. & Hunter, T. (1988), *Science*, 241, 52). Comparative sequences shown are for human Ret (Takahashi, M. & Cooper, G. M. (1987). *Mol.Cell.Biol.*, 7, 1378–1385), and Jtk14 (Partanen, J., Mäkelä, T. P., Alitalo, R., Lehväslaiho, H. & Alitalo, K. (1990) *Proc.Natl.Acad.Sci.*, 87, 8913–8917) and murine Flg (Reid, H. H., Wilks, A. F. & Bernard, O. (1990) *Proc.Natl.Acad.Sci.*, 87, 1596–1600).

As shown in FIG. 14, the putative kinase domain contains several sequence motifs conserved among tyrosine kinases, including the tripeptide motif DFG, which is found in almost all known kinases, and the consensus ATP-binding site motifs GXGXXG followed by AXK 16 amino acid residues downstream (Hanks et al., 1988). Transmembrane RTK's posses a methionine residue within the motif WMAIESL of conserved region VIII of the catalytic domain (Hanks et al., 1988) as does tek, and the catalytic domain is interrupted by a putative 21 amino acid kinase insert, a structural motif not found in cytoplasmic tyrosine kinases (Hanks et al., 1988).

Comparison with other tyrosine kinases (FIG. 14) reveals that the deduced tek amino acid sequence shows 42% sequence identity to the mouse fibroblast growth factor receptor Flg (Reid et al., 1990; Safran, A., Avivi, A., Orr-Urtereger, A., Neufeld, G., Lonai, P., Givol, D. & Yarden, Y. (1990). *Oncogene*5, 635–643, Sambrook, J., Fritsch, E. F. & Maniatis, T. (1989). *Molecular Cloning*. Cold Spring Harbor Laboratory Press) and 45% to the transmembrane RTK encoded by the human c-ret protooncogene (Takahashi & Cooper, 1987). In addition, striking sequence identity is observed to a 65 amino acid residue sequence encoded by Jtk14, a putative tyrosine kinase cDNA isolated from differentiating human K562 cells by RT-PCR (Partanen et al., 1990). Taken together, the results suggest that tek encodes a novel RTK.

EXAMPLE II

Chromosomal Mapping of the Tek Locus

Mapping of the tek locus was accomplished by monitoring the strain distribution pattern of an AccI restriction site polymorphism in recombinant inbred (RI) mouse strains derived from matings between AKR/J (A) and DBA/2J (D) mice. The tek cDNA detects bands of 6.5, 6.1, 1.3 and 6.5, 3.1, 1.3 kb in DNA from the A and D strains, respectively. Southern blot hybridization analysis of DNA from 24 RI mice with the 1.6 kb cDNA probe, and comparison of the segregation pattern with the Jackson Laboratory data base, revealed 95.8% cosegregation between tek and both brown and pmv-23, two loci that have previously been localized to mouse chromosome 4 (Lyon & Searle, 1989). Table 2 shows the cosegregation of the tek, brown, and pmv-23 loci in A×D strains. In Table 2 for each RI strain, the symbol shown indicates the presence of an allele characteristic of the progenitor from which the strain was derived (A, AKR/J; D, DBA/2J) These data place tek between the brown and pmv-23 loci within 3.8±1.9 centimorgans of each interval.

EXAMPLE III

Figure 5:
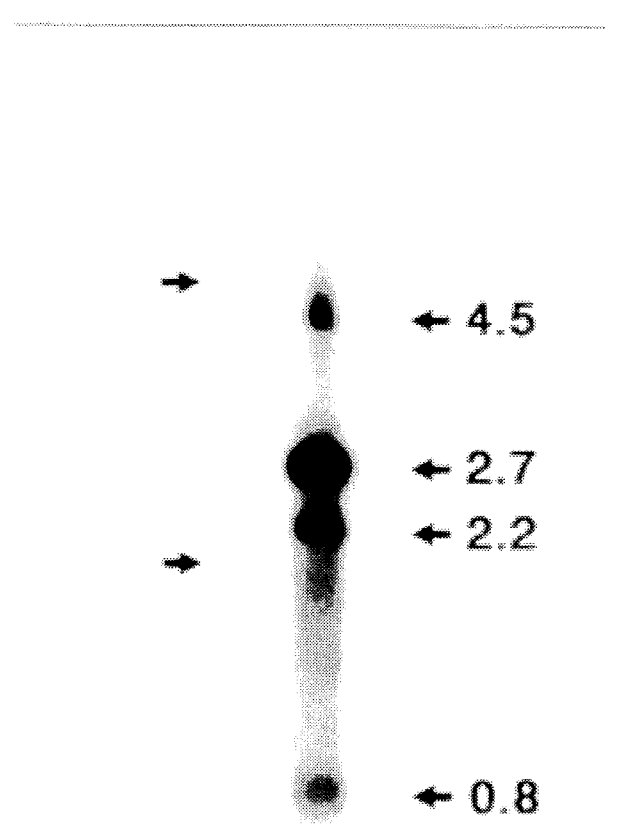
FIG. 5 shows a Northern blot hybridization analysis of expression of tek in 12.5 day murine embryonic heart.

Multiple Tek-related Transcripts are Expressed in Embryonic Heart tek expression in embryonic heart was examined by Northern blot hybridization using an antisense probe derived from the 1.6 kb tek cDNA. FIG. 5 shows a Northern blot hybridization analysis of tek expression in 12.5 day murine embryonic heart; Arrows on the left denote the position of migration of 28 S and 18 S ribsomal RNAs obtained from adjacent lane loaded with total RNA.

FIG. 5 shows that the tek probe detects 4 transcripts of 4.5, 2.7, 2.2, and 0.8 kb in size in cardiac RNA from 12.5 day mouse embryos. These hybridizing species vary considerably in signal intensity, suggesting that they may differ in relative abundance, with expression of the 2.7 and 2.2 kb transcripts occurring at significantly higher levels than the 4.5 and 0.8 kb RNAs. While the exact relationship among these transcripts is unclear, it is possible that they arise by differential splicing, since the 1.6 kb tek cDNA detects a single genomic locus in mouse DNA by Southern blot hybridization at the same stringency.

EXAMPLE IV

In Situ Localization of Tek Expression during Mouse Embryogenesis

To determine which cell types express tek during development, RNA in situ hybridization analyses were performed on mouse embryos with an antisense riboprobe synthesized from the 1.6 kb tek cDNA.

Figure 6:
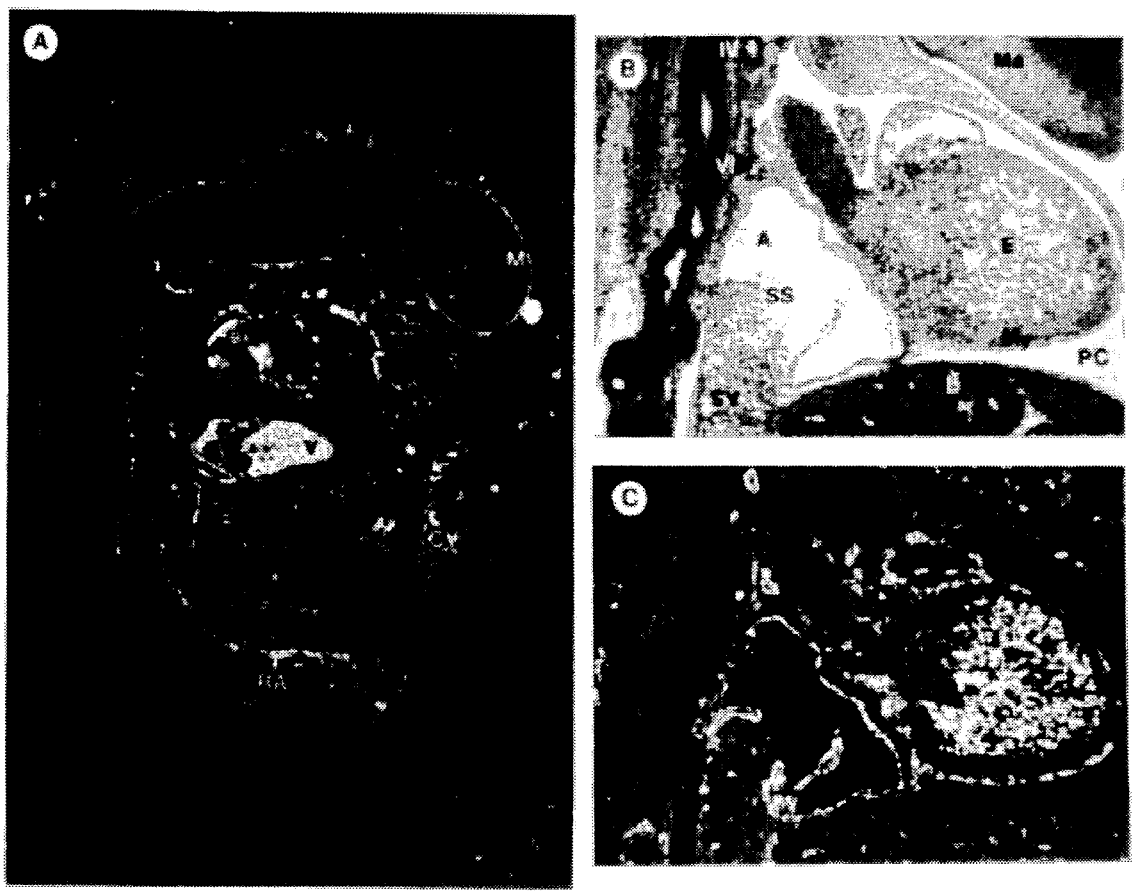
FIG. 6 shows the in situ hybridization analysis of expression of tek in the 12.5 day embryo.

FIG. 6 shows the in situ hybridization analysis of tek expression in the 12.5 day embryo; A. Dark field illumination of a para-sagittal section. Bar: 600 µm. B. and C. Bright and dark field illumination respectively, of the heart region taken from a mid-sagittal section. Bar: 300 µm. IV and VI, fourth and sixth aortic arches; A, atrium; BA, basilar artery; CV, caudal vein; E, endocardium; L, liver; M, leptomeninges; Ma, mandible; My, myocardium; PC, pericardial cavity; RA, renal artery; SS, sino-auricular septum; SV, sinus venosus; V, ventricle.

FIG. 6A shows that in 12.5 day mouse embryos, expression of tek is readily detected in the heart, the leptomeninges lining the brain and spinal cord, and the inner lining of major blood vessels, including the caudal vein and basilar and renal arteries. In addition, thin bands of hybridization are observed in the intersomite regions, corresponding to tek expression in the intersegmental vessels. Close examination of the region of the developing heart (FIGS. 6B and 6C) reveals that tek is expressed in the endocardium, as well as in cells lining the lumina of the atria, the IV and VI aortic arches, the sinus venosus, and the sino-auricular septum. In addition, tek expression is observed in numerous small blood vessels perforating the liver and mandible. These observations, together with the overall pattern of hybridization seen in the 12.5 day embryo, demonstrate that tek is expressed in the endothelial cells of the tunica interna, the innermost lining of the blood vessels; hence the designation tunica interna endothelial cell kinase, tek.

More detailed information on tek expression was obtained through analysis of sections from earlier developmental stages. Hybridization to 6.5 and 7 day embryos revealed that while tek is expressed strongly in the inner lining of the small blood vessels and capillaries of the maternal decidua, no expression is observed in either the embryo itself or the ectoplacental cone. The absence of tek expression at these stages is consistent with the fact that at 6.5 to 7 days the embryo contains only a small amount of mesoderm from which endothelial cells are known to be derived.

Figure 7:
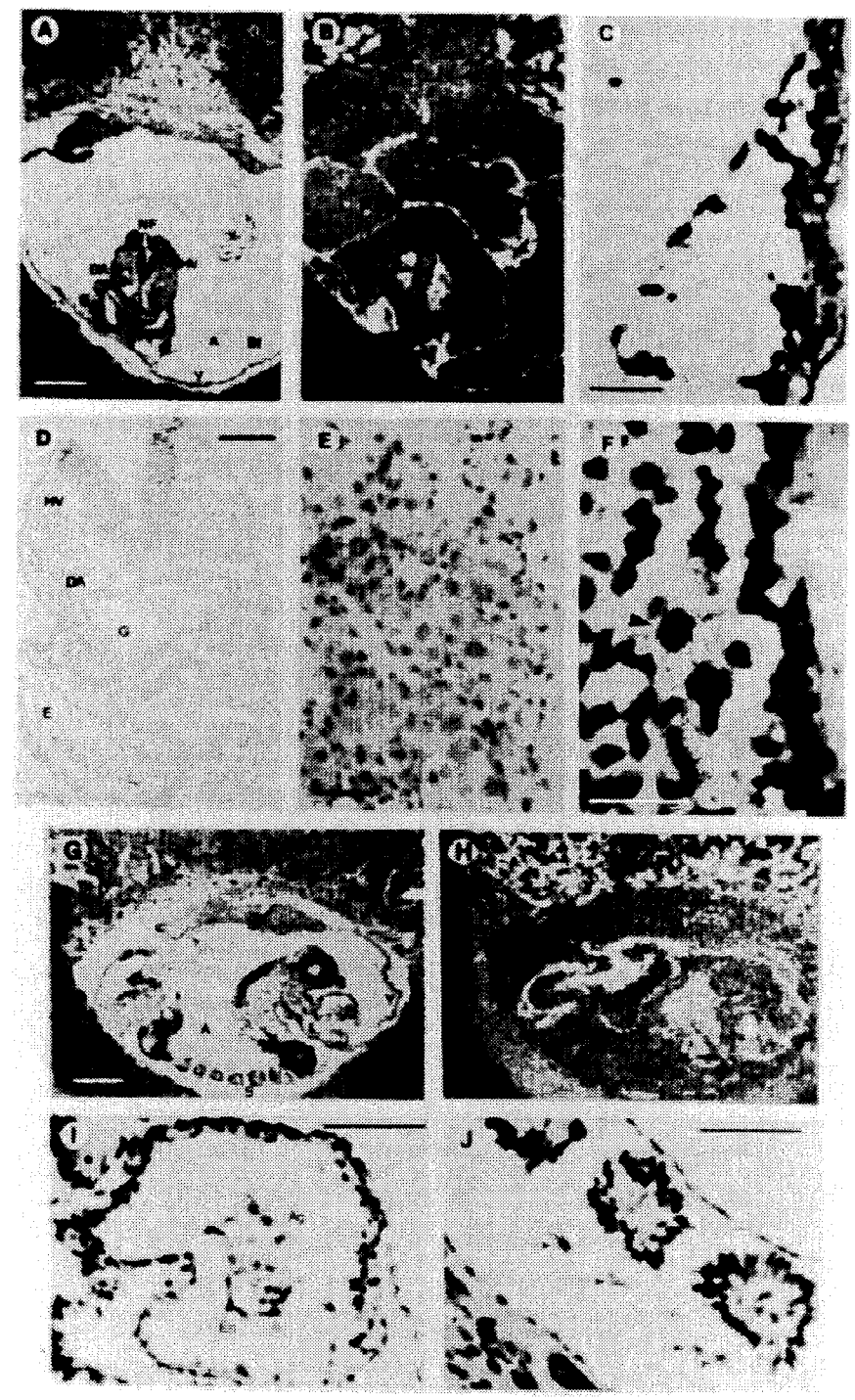
FIG. 7 shows the expression of tek precedes that of von Willebrand factor in 8.5 day embryos.

FIG. 7 shows the expression of tek precedes that of von Willebrand factor in 8.5 day embryos; Adjacent transverse sections through an 8.5 day embryo fixed in utero were either hybridized in situ with an [$^{35}$S]-labelled tek probe or stained immunohistochemically for von Willebrand factor. A. Bright field illumination of tek expression, Bar: 300 µm. B. Dark field illumination of section in A. C. High magnification of a blood island, slightly out of the field shown in A, depicting silver grains over flat, elongated cells of endothelial-like morphology, Bar: 50 µm. D. Adjacent section to A at higher magnification showing absence of expression of von Willebrand factor in the embryo, Bar: 100 µm. E. Adjacent section to A at higher magnification showing expression of von Willebrand factor in the endothelial lining of the blood vessels of the maternal decidua. Bar: 200 µm. F. High magnification of cephalic region in A showing silver grains over a large, round cell of angioblast-like morphology (arrow). Bar: 50 µm. G. Bright field illumination of a sagittal section of an 8.5 day embryo hybridized in situ with an

[$^{35}$S]-labelled tek probe. Bar: 300 μm. H. Dark field illumination of G. I. Higher magnification of heart region in A showing silver grains over cells with endothelial- and angioblast-like morphology in the developing endocardium. Bar: 100 μm. J. Higher magnification of somite region in A showing tek-expressing cells extending beneath, and possibly from, the ventral surface of the somites. Bar: 100 μm. A, amnion; Ag, presumptive angioblast; BI, blood island; D, maternal decidua; DA, dorsal aorta; E, endocardium; Ec, ectoplacental cone; En, endothelial cell; G, foregut; HV, head vein; NF, neural fold; S, somite; Y, yolk sac.

RNA in situ analysis of 8.0 day embryos revealed that tek expression first becomes detectable in the developing yolk sac and a few small clusters of cells in the cephalic mesenchyme. This expression becomes more pronounced by Day 8.5, at which time significant hybridization can be observed in the mesodermal component of the amnion (outer cell layer) and yolk sac (inner cell layer), as well as in the developing endocardium and the inner lining of the head veins and dorsal aortae (FIGS. 7A and 7B). In addition, sagittal sections reveal numerous focal areas of hybridization throughout the cephalic mesenchyme in regions thought to contain developing vasculature, as well as a small number of tek-expressing cells extending beneath the ventral surface of the somites (FIGS. 7H and 7J).

Figure 8:
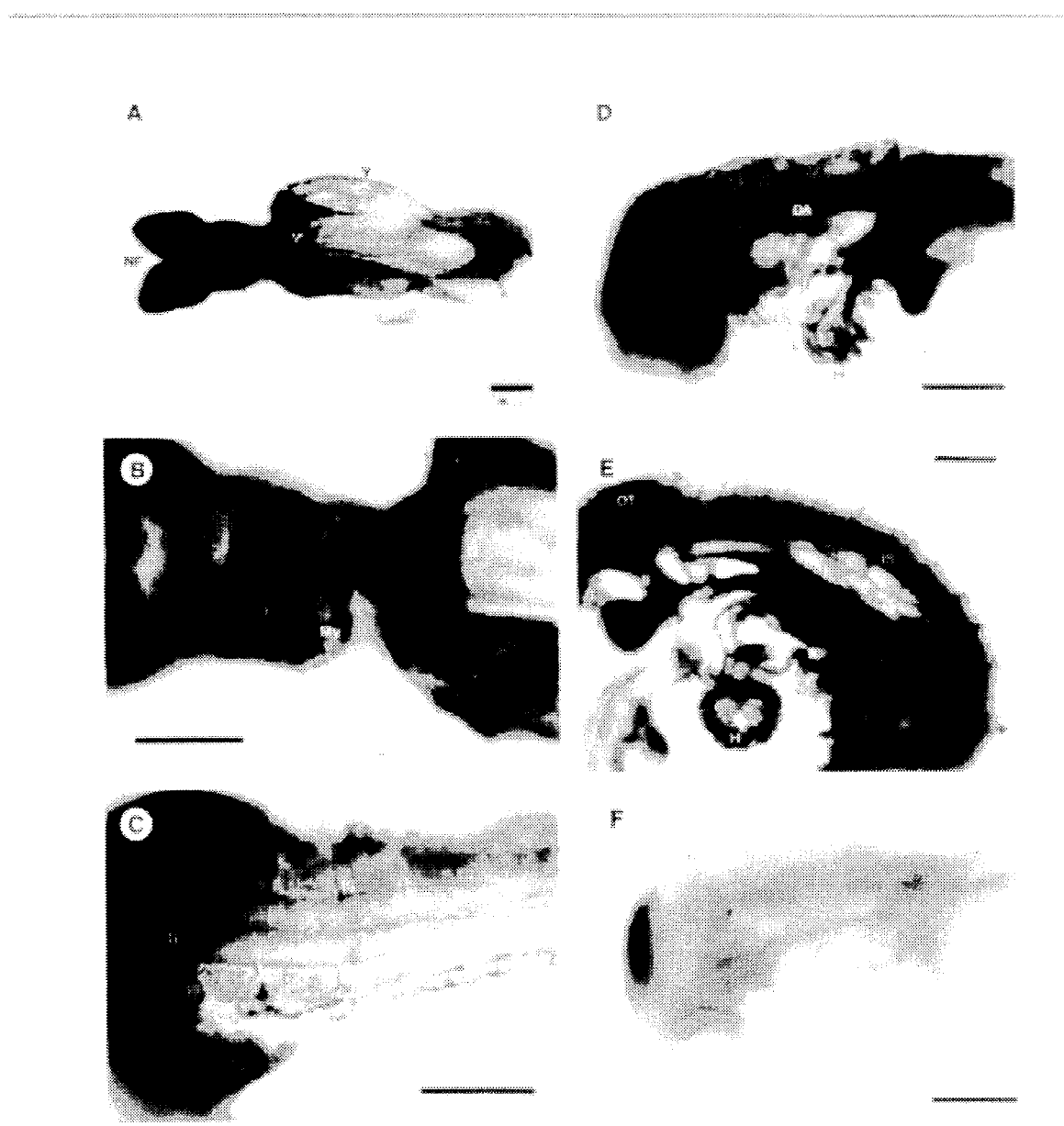
FIG. 8 shows expression of tek in whole mount embryos (A., B., and C.); expression in Day 8.0 embryos (D.); mRNA distribution in a Day 9.5 embryo (E.); and En2 expression in a Day 8 embryo (F.)

Whole mount in situ hybridization analysis confirmed and extended the above observations, as well as provided a three dimensional perspective on tek expression during embryogenesis. FIG. 8 shows tek expression in whole mount embryos; A., B., C. and D. tek expression in Day 8.0 embryos. E. tek mRNA distribution in a Day 9.5 embryo. F. En2 expression in a Day 8 embryo. I, II, III, first, second and third aortic arches; DA. dorsal aorta; E, endocardium; G, foregut pocket; H, heart; IS, intersegmental vessel; My, myocardium; NF, neural fold; OT; otic vesicle; V, vitelline vein; Y, yolk sac. Bars: 250 μm.

Consistent with our observations with sectioned material, localized tek expression was not observed on embryonic Day 7. The first detectable expression was seen about the time of first somite formation when signal was observed in the yolk sac, head mesenchyme, and heart. In Day 8.5 embryos, tek was found to be expressed in these same areas, and in the paired dorsal aortae, the vitelline veins, and in the forming intersegmental vessels (FIG. 8). By this time, tek expression was clearly confined to blood vessels within the embryo. On Day 9, tek expression was seen in addition, in the aortic arches and expression was very striking in the endocardium (FIG. 8E). Control hybridizations with an En-2 probe demonstrated the specificity of tek RNA detection (FIG. 8F).

EXAMPLE V

Expression of Tek in Endothelial Cell Progenitors

The observation that tek is expressed between Day 8.0 and 8.5 in focal regions thought to represent developing blood vessels raised the possibility that tek might be expressed in endothelial cell progenitors. Indeed, close inspection of hybridized sections from 8 to 8.5 day embryos revealed that while the expression of tek in the maternal decidua is restricted to cells of an endothelial cell morphology, tek expressing cells in the embryo are of two morphologically distinct cell types. In the developing blood islands of the yolk sac, where tek expression is first detected, silver grains are localized predominantly to elongated cells with characteristic endothelial cell morphology (FIG. 7C). In contrast, within the cephalic mesenchyme, silver grains are frequently observed over large, round cells that, on the basis of similar morphology to cells described during avian embryogenesis (Pardanaud et al., 1987; Coffin & Poole, 1988; Noden, 1989; Noden, 1991), correspond to angioblasts, the presumptive progenitor of endothelial cells (FIG. 7F). Both cell types are observed in the developing endocardium (FIG. 7I) which, at later stages, is known to contain only fully mature endothelial cells.

To characterize more precisely the staging of tek expression within the endothelial lineage, sections adjacent to those used for in situ hybridization were stained immunohistochemically for von Willebrand factor, a well characterized marker of mature endothelial cells (Jaffe, E. A., Hoyer, L. W. & Nachman, R. L. (1973). *J. Clin. Invest.,* 52, 2757–2764; Hormia, M., Lehto, V.-P. & Virtanen, I. (1984), *Eur. J. Cell. Biol.,* 33, 217–228). FIGS. 7B and H shows that whereas tek is expressed in both the maternal decidua and the embryo at Day 8.5, expression of von Willebrand factor is observed only in the tek-expressing, vascular endothelial cells of the maternal decidua (FIGS. 7D and 7E). Hence tek expression precedes that of von Willebrand factor during embryogenesis. The same scenario is observed at later developmental stages during vascularization of individual organs.

Figure 9:
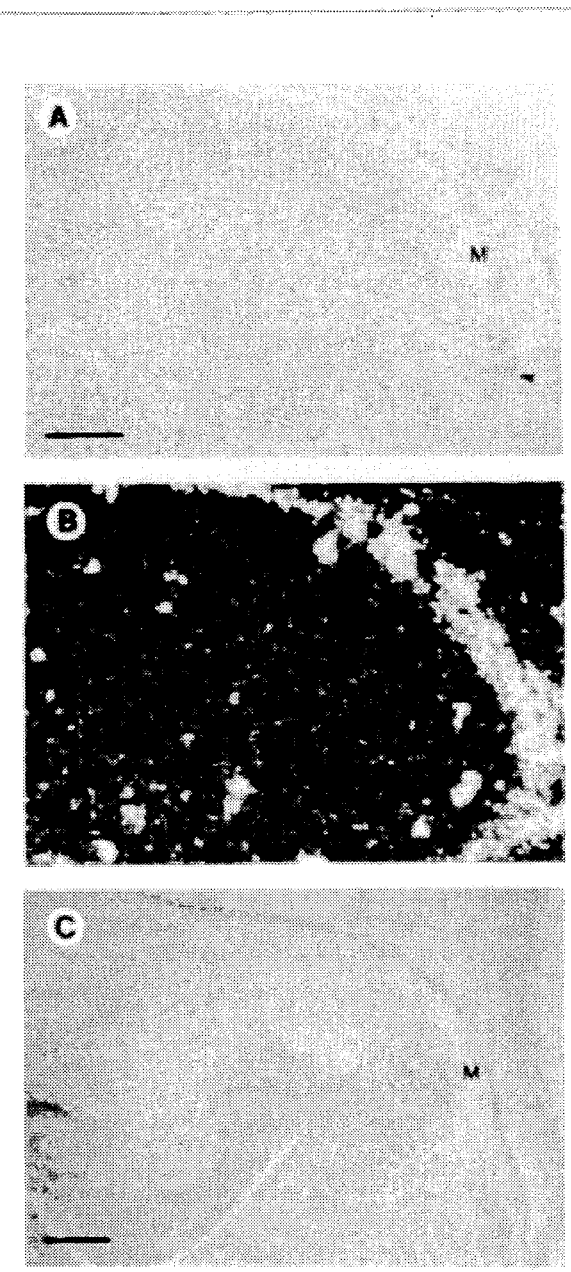
FIG. 9 shows the expression of tek precedes that of von Willebrand factor in the developing leptomeninges and in particular the absence of immunohistochemical staining of von Willebrand factor in Day 12.5 leptomeninges (A); in situ detection of tek expression in Day 12.5 leptomeninges (B); staining of von Willebrand factor in Day 14.5 leptomeninges (C)

FIG. 9 shows the expression of tek precedes that of von Willebrand factor in the developing leptomeninges; A. Absence of immunohistochemical staining of von Willebrand factor in Day 12.5 leptomeninges. Arrow denotes a large blood vessel faintly positive for von Willebrand factor. B. In situ detection of tek expression in Day 12.5 leptomeninges. C. Staining of von Willebrand factor in Day 14.5 leptomeninges. Day 14.5 leptomeninges were positive for tek expression (not shown). M, leptomeninges. Bars: 200 μm.

FIG. 9 shows that in the 12.5 day embryo, the developing leptomeninges hybridizes strongly with tek but fails to stain positive for von Willebrand factor. By Day 14.5, however, expression of von Willebrand factor can be readily detected in the leptomeninges. Assuming that there is not a significant lag between transcription and translation of von Willebrand factor, these observations, together with those on the morphology of tek-expressing cells, suggest that tek is expressed in both mature endothelial cells and their progenitors.

EXAMPLE VI

Tek is Expressed in Adult Vasculature

While the above results establish that tek is expressed during vascularization of the embryo, it was also of interest to determine whether expression of tek is maintained in endothelial cells of the adult. In situ hybridization analysis of a section through the heart region of a 3 week-old mouse revealed that tek is expressed in the endocardium as well as in the endothelial lining of major blood vessels, both arteries and veins, connecting with the adult heart (FIG. 10).

Figure 10:
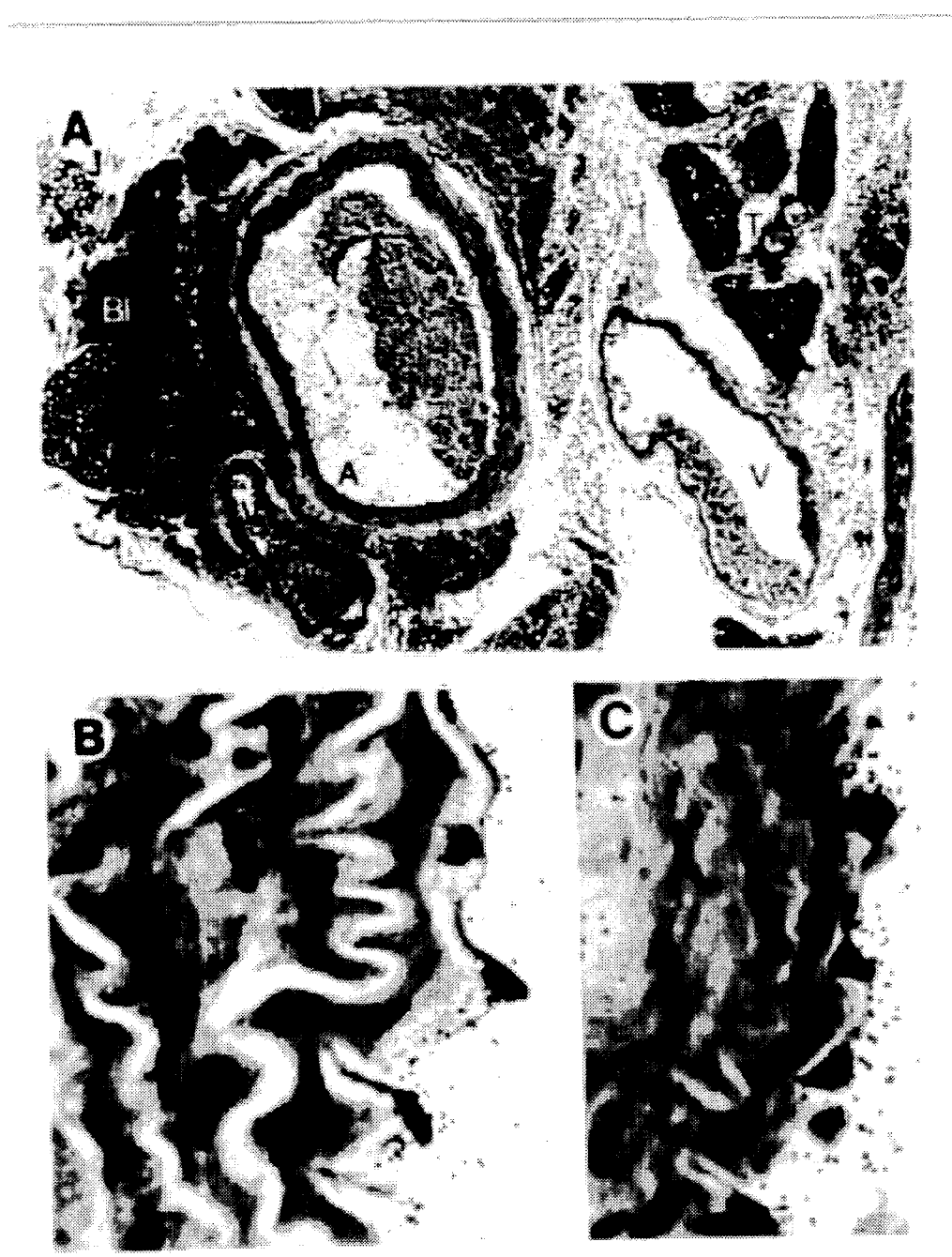
FIG. 10 shows the expression of tek in adult vasculature and in particular bright field illumination of a section through the upper heart region of a 3 week-old mouse hybridized with an [$^{35}$S]-labelled tek probe (B); bright field illumination showing tek expression in endothelial cells lining the artery and vein respectively (C)

FIG. 10 shows the expression of tek in adult vasculature. A. Bright field illumination of a section through the upper heart region of a 3 week-old mouse hybridized with an [$^{35}$S]-labelled tek probe. Bar: 20 μm. B. and C.

Bright field illumination showing tek expression in endothelial cells lining the artery and vein respectively. Bar: 1 μm. Immunohistochemical staining of adjacent sections revealed that structures positive for tek expression also stained positive for von Willebrand factor. A, artery; Bl, extravasated blood; T, trachea; V, vein.).

The intensity of the hybridization signal observed for these structures is considerably lower than that observed for the endocardium and blood vessels of 12.5 day embryos hybridized and processed in parallel. This could indicate that mature endothelial cells, which are thought to be resting, have a different quantitative or qualitative requirement for expression of tek.

EXAMPLE VII

Determination of the Initiation Site of Translation of Tek

Additional cDNA sequences spanning the entire tek cDNA were obtained by screening cDNA libraries using well established protocols (Sambrook et al, 1989, Molecular Cloning, A Laboratory Manual Cold Spring Harbor Lab. Press). Analysis of the complete cDNA sequence allowed determination of the most probable start of translation for the following reasons: (1) The putative initiation codon (Methionine) is followed by a stretch of 23 amino acids which are of sufficient hydrophobicity that they could serve as a signal peptide. (2) The reading frame does not contain any stop codons for 1118 amino acids and the derived amino acid sequence contains primary sequence motifs that are characteristic of receptor tyrosine kinases. (3) the other two forward reading frames are not open for any significant distance and contain multiple stop codons.

EXAMPLE VIII

Figure 12:
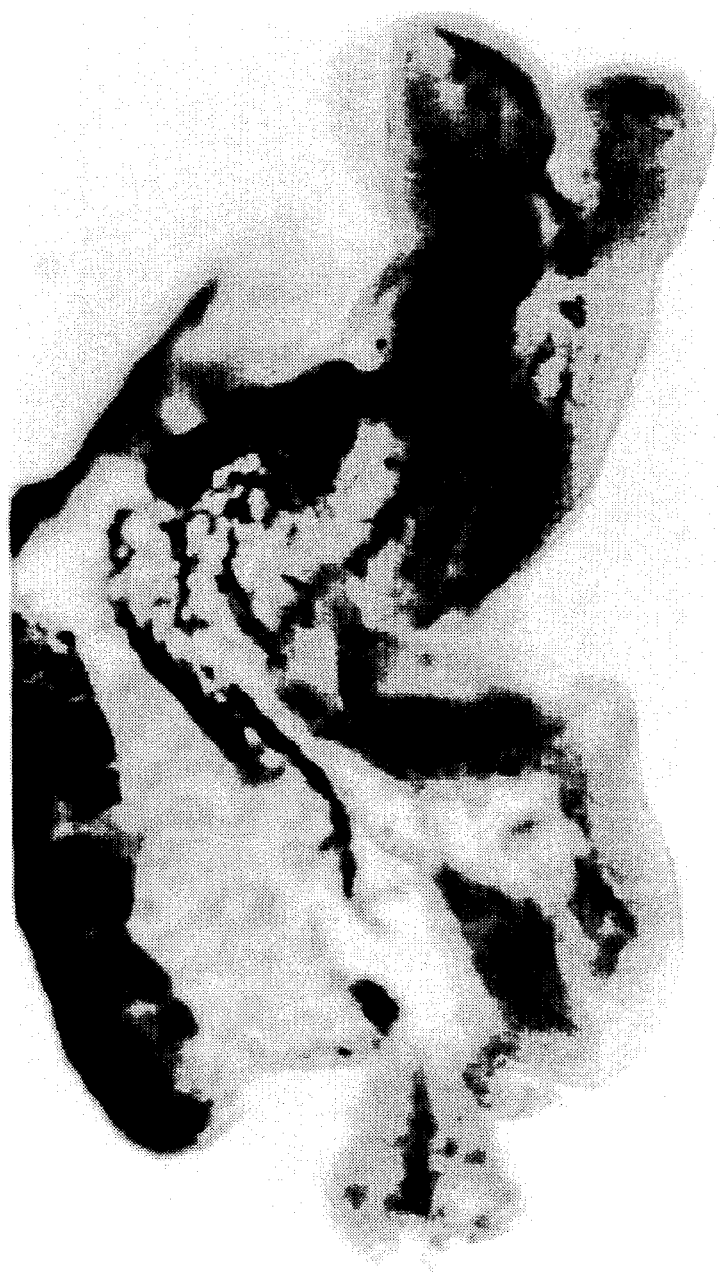
FIG. 12 shows expression of LacZ in Day 8.5 embryos produced using a DNA construct comprising the transcriptional regulatory element of the invention and LacZ.
Figure 13:
FIG. 13 shows tek mRNA distribution in a Day 8.5 embryo.

A DNA segment was isolated from a mouse genomic bacteriophage library using a 5'-prime probe, consisting of nucleotides 0 to 912 of the tek cDNA, which contained the initiation codon and untranslated sequences of tek using the procedures of Sambrook et al., 1989, Molecular Cloning, A Laboratory Manual. Cold Spring Harbour Lab. Press. The DNA segment was cloned in the plasmid pGEm72F+ and propagated in *coli* 12. A 16 kb phage clone was shown by hybridization with this 5'-prime probe and sequence analysis using oligonucleotides specific for the cDNA sequence and the plasmid backbone, to contain a single exon with 175 bp homologous to the cDNA. A DNA fragment extending from the Bgl II restriction site located at nucleotide 110 of the cDNA to the nearest Kpn I in the phage was cloned upstream of the bacterial gene lacZ. This reporter construct containing 7.2 kb of the tek gene was microinjected into pronuclei of fertilized randomly bred CD-1 mice using procedures as set out in Hogan et al., 1986, Manipulating the Mouse Embryo, A Laboratory Manual. Cold Spring Harbor Lab. Press. Three transgenic founder embryos were dissected from their foster mothers and yolk sac DNA analyzed for the presence of the transgene. Expression of the transgene was determined by the X-gal staining of whole embryos and subsequent sectioning of the embryos. FIG. 12 shows expression of LacZ in Day 8.5 embryos and FIG. 13 shows mRNA distribution in a Day 8.5 embryo. The 7.2 kb fragment was able to drive lacZ expression in endothelial cells that had previously been shown to express tek RNA (FIG. 12) thus demonstrating that this DNA contained the tek promoter.

TABLE 1

| Protein tyrosine kinase cDNAs is isolated by RT-PCR | | | | | |
|---|---|---|---|---|---|
| Embryonic Age | cDNA | | | | |
| (Days) | tek | pdgfrb | c-abl | c-sre | bmk |
| 9.5 | 26 | 7 | 2 | 1 | 1 |
| 12.5 | 5 | 10 | — | — | — |

TABLE 2

| Cosegregation of the tek, brown, and pmv-23 loci in A x D strains. | | | | | | | | | | | | | | | | | | | | | | |
|---|---|---|---|---|---|---|---|---|---|---|---|---|---|---|---|---|---|---|---|---|---|---|
| | A x D strain | | | | | | | | | | | | | | | | | | | | | | |
| Locus | 1 | 2 | 3 | 6 | 7 | 8 | 9 | 10 | 11 | 12 | 13 | 14 | 15 | 16 | 18 | 20 | 21 | 22 | 23 | 24 | 25 | 26 | 27 | 28 |
| tek | D | D | A | D | D | A | A | A | D | A | D | A | D | D | D | D | A | D | D | A | D | D | D | D |
| brown | D | D | A | D | D | A | A | A | D | A | A | A | D | D | D | A | D | A | A | D | D | D | D |
| pmv-23 | D | D | A | D | D | A | D | A | D | A | D | D | D | A | D | D | A | D | D | A | D | D | D | A |

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 4175 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Mus pahari
        ( B ) STRAIN: CD-1
        ( D ) DEVELOPMENTAL STAGE: Embryo
        ( F ) TISSUE TYPE: Heart ( v i i ) IMMEDIATE SOURCE:
        ( B ) CLONE: tck ( v i i i ) POSITION IN GENOME:
        ( A ) CHROMOSOME/SEGMENT: 4
        ( B ) MAP POSITION: Between the brown and pmv-23 loci ( i x ) FEATURE:
        ( A ) NAME/KEY: CDS
        ( B ) LOCATION: 124..3477
        ( D ) OTHER INFORMATION: /function="putative transmembrane
            receptor"
        / product="tyrosine kinase"
        / gene="tck"
        / standard_name="tyrosine kinase receptor protein"

( x i ) SEQUENCE DESCRIPTION: SEQ ID NO:1:

```
GCCAACTTGT AAACAAGAGC GAGTGGACCA TGCGAGCGGG AAGTCGCAAA GTTGTGAGTT        60

GTTGAAAGCT TCCCAGGGAC TCATGCTCAT CTGTGGACGC TGGATGGGGA GATCTGGGGA       120

AGT ATG GAC TCT TTA GCC GGC TTA GTT CTC TGT GGA GTC AGC TTG CTC        168
    Met Asp Ser Leu Ala Gly Leu Val Leu Cys Gly Val Ser Leu Leu
    1               5                   10                  15

CTT TAT GGA GTA GTA GAA GGC GCC ATG GAC CTG ATC TTG ATC AAT TCC        216
Leu Tyr Gly Val Val Glu Gly Ala Met Asp Leu Ile Leu Ile Asn Ser
                20                  25                  30

CTA CCT CTT GTG TCT GAT GCC GAA ACA TCC CTC ACC TGC ATT GCC TCT        264
Leu Pro Leu Val Ser Asp Ala Glu Thr Ser Leu Thr Cys Ile Ala Ser
                35                  40                  45

GGG TGG CAC CCC CAT GAG CCC ATC ACC ATA GGA AGG GAC TTT GAA GCC        312
Gly Trp His Pro His Glu Pro Ile Thr Ile Gly Arg Asp Phe Glu Ala
            50              55                  60

TTA ATG AAC CAG CAC CAA GAT CCA CTG GAG GTT ACT CAA GAT GTG ACC        360
Leu Met Asn Gln His Gln Asp Pro Leu Glu Val Thr Gln Asp Val Thr
    65                  70                  75

AGA GAA TGG GCG AAA AAA GTT GTT TGG AAG AGA GAA AAG GCC AGT AAG        408
Arg Glu Trp Ala Lys Lys Val Val Trp Lys Arg Glu Lys Ala Ser Lys
80              85                  90                      95

ATT AAT GGT GCT TAT TTC TGT GAA GGT CGA GTT CGA GGA CAG GCT ATA        456
Ile Asn Gly Ala Tyr Phe Cys Glu Gly Arg Val Arg Gly Gln Ala Ile
                100                 105                 110
```

```
AGG ATA CGG ACC ATG AAG ATG CGT CAA CAA GCA TCC TTC CTA CCT GCT      504
Arg Ile Arg Thr Met Lys Met Arg Gln Gln Ala Ser Phe Leu Pro Ala
            115             120                 125

ACT TTA ACT ATG ACC GTG GAC AGG GGA GAT AAT GTG AAC ATA TCT TTC      552
Thr Leu Thr Met Thr Val Asp Arg Gly Asp Asn Val Asn Ile Ser Phe
            130             135                 140

AAA AAG GTG TTA ATT AAA GAA GAA GAT GCA GTG ATT TAC AAA AAT GGC      600
Lys Lys Val Leu Ile Lys Glu Glu Asp Ala Val Ile Tyr Lys Asn Gly
        145             150                 155

TCC TTC ATC CAC TCA GTG CCC CGG CAT GAA GTA CCT GAT ATT TTA GAA      648
Ser Phe Ile His Ser Val Pro Arg His Glu Val Pro Asp Ile Leu Glu
160             165                 170                 175

GTT CAC TTG CCG CAT GCT CAG CCC CAG GAT GCT GGT GTG TAC TCG GCC      696
Val His Leu Pro His Ala Gln Pro Gln Asp Ala Gly Val Tyr Ser Ala
                    180                 185                 190

AGG TAC ATA GGA GGA AAC CTG TTC ACC TCA GCC TTC ACC AGG CTG ATT      744
Arg Tyr Ile Gly Gly Asn Leu Phe Thr Ser Ala Phe Thr Arg Leu Ile
                195                 200                 205

GTT CGG AGA TGT GAA GCT CAG AAG TGG GGG CCC GAC TGT AGC CGT CCT      792
Val Arg Arg Cys Glu Ala Gln Lys Trp Gly Pro Asp Cys Ser Arg Pro
            210                 215                 220

TGT ACT ACT TGC AAG AAC AAT GGA GTC TGC CAT GAA GAT ACC GGG GAA      840
Cys Thr Thr Cys Lys Asn Asn Gly Val Cys His Glu Asp Thr Gly Glu
            225             230                 235

TGC ATT TGC CCT CCT GGG TTT ATG GGG AGA ACA TGT GAG AAA GCT TGT      888
Cys Ile Cys Pro Pro Gly Phe Met Gly Arg Thr Cys Glu Lys Ala Cys
240             245                 250                 255

GAG CCG CAC ACA TTT GGC AGG ACC TGT AAA GAA AGG TGT AGT GGA CCA      936
Glu Pro His Thr Phe Gly Arg Thr Cys Lys Glu Arg Cys Ser Gly Pro
                    260                 265                 270

GAA GGA TGC AAG TCT TAT GTG TTC TGT CTC CCA GAC CCT TAC GGG TGT      984
Glu Gly Cys Lys Ser Tyr Val Phe Cys Leu Pro Asp Pro Tyr Gly Cys
                275                 280                 285

TCC TGT GCC ACA GGC TGG AGG GGG TTG CAG TGC AAT GAA GCA TGC CCA     1032
Ser Cys Ala Thr Gly Trp Arg Gly Leu Gln Cys Asn Glu Ala Cys Pro
            290                 295                 300

TCT GGT TAC TAC GGA CCA GAC TGT AAG CTC AGG TGC CAC TGT ACC AAT     1080
Ser Gly Tyr Tyr Gly Pro Asp Cys Lys Leu Arg Cys His Cys Thr Asn
    305                 310                 315

GAA GAG ATA TGT GAT CGG TTC CAA GGA TGC CTC TGC TCT CAA GGA TGG     1128
Glu Glu Ile Cys Asp Arg Phe Gln Gly Cys Leu Cys Ser Gln Gly Trp
320             325                 330                 335

CAA GGG CTG CAG TGT GAG AAA GAA GGC AGG CCA AGG ATG ACT CCA CAG     1176
Gln Gly Leu Gln Cys Glu Lys Glu Gly Arg Pro Arg Met Thr Pro Gln
            340                 345                 350

ATA GAG GAT TTG CCA GAT CAC ATT GAA GTA AAC AGT GGA AAA TTT AAC     1224
Ile Glu Asp Leu Pro Asp His Ile Glu Val Asn Ser Gly Lys Phe Asn
            355                 360                 365

CCC ATC TGC AAA GCC TCT GGG TGG CCA CTA CCT ACT AGT GAA GAA ATG     1272
Pro Ile Cys Lys Ala Ser Gly Trp Pro Leu Pro Thr Ser Glu Glu Met
        370                 375                 380

ACC CTA GTG AAG CCA GAT GGG ACA GTG CTC CAA CCA AAT GAC TTC AAC     1320
Thr Leu Val Lys Pro Asp Gly Thr Val Leu Gln Pro Asn Asp Phe Asn
        385                 390                 395

TAT ACA GAT CGT TTC TCA GTG GCC ATA TTC ACT GTC AAC CGA GTC TTA     1368
Tyr Thr Asp Arg Phe Ser Val Ala Ile Phe Thr Val Asn Arg Val Leu
400             405                 410                 415

CCT CCT GAC TCA GGA GTC TGG GTC TGC AGT GTG AAC ACA GTG GCT GGG     1416
Pro Pro Asp Ser Gly Val Trp Val Cys Ser Val Asn Thr Val Ala Gly
```

-continued

| | | | | | 420 | | | | | 425 | | | | | 430 | | |
|---|---|---|---|---|---|---|---|---|---|---|---|---|---|---|---|---|---|
| ATG | GTG | GAA | AAG | CCT | TTC | AAC | ATT | TCC | GTC | AAA | GTT | CTT | CCA | GAG | CCC | | 1464 |
| Met | Val | Glu | Lys | Pro | Phe | Asn | Ile | Ser | Val | Lys | Val | Leu | Pro | Glu | Pro | | |
| | | | 435 | | | | | 440 | | | | | 445 | | | | |
| CTG | CAC | GCC | CCA | AAT | GTG | ATT | GAC | ACT | GGA | CAT | AAC | TTT | GCT | ATC | ATC | | 1512 |
| Leu | His | Ala | Pro | Asn | Val | Ile | Asp | Thr | Gly | His | Asn | Phe | Ala | Ile | Ile | | |
| | | 450 | | | | | 455 | | | | | 460 | | | | | |
| AAT | ATC | AGC | TCT | GAG | CCT | TAC | TTT | GGG | GAT | GGA | CCC | ATC | AAA | TCC | AAG | | 1560 |
| Asn | Ile | Ser | Ser | Glu | Pro | Tyr | Phe | Gly | Asp | Gly | Pro | Ile | Lys | Ser | Lys | | |
| | 465 | | | | | 470 | | | | | 475 | | | | | | |
| AAG | CTT | TTC | TAT | AAA | CCT | GTC | AAT | CAG | GCC | TGG | AAA | TAC | ATT | GAA | GTG | | 1608 |
| Lys | Leu | Phe | Tyr | Lys | Pro | Val | Asn | Gln | Ala | Trp | Lys | Tyr | Ile | Glu | Val | | |
| 480 | | | | | 485 | | | | | 490 | | | | | 495 | | |
| ACG | AAT | GAG | ATT | TTC | ACT | CTC | AAC | TAC | TTG | GAG | CCG | CGG | ACT | GAC | TAC | | 1656 |
| Thr | Asn | Glu | Ile | Phe | Thr | Leu | Asn | Tyr | Leu | Glu | Pro | Arg | Thr | Asp | Tyr | | |
| | | | | 500 | | | | | 505 | | | | | 510 | | | |
| GAG | CTG | TGT | GTG | CAG | CTG | GCC | CGT | CCT | GGA | GAG | GGT | GGA | GAA | GGG | CAT | | 1704 |
| Glu | Leu | Cys | Val | Gln | Leu | Ala | Arg | Pro | Gly | Glu | Gly | Gly | Glu | Gly | His | | |
| | | | 515 | | | | | 520 | | | | | 525 | | | | |
| CCT | GGG | CCT | GTG | AGA | CGA | TTT | ACA | ACA | GCG | TGT | ATC | GGA | CTC | CCT | CCT | | 1752 |
| Pro | Gly | Pro | Val | Arg | Arg | Phe | Thr | Thr | Ala | Cys | Ile | Gly | Leu | Pro | Pro | | |
| | | 530 | | | | | 535 | | | | | 540 | | | | | |
| CCA | AGA | GGT | CTC | AGT | CTC | CTG | CCA | AAA | AGC | CAG | ACA | GCT | CTA | AAT | TTG | | 1800 |
| Pro | Arg | Gly | Leu | Ser | Leu | Leu | Pro | Lys | Ser | Gln | Thr | Ala | Leu | Asn | Leu | | |
| | 545 | | | | | 550 | | | | | 555 | | | | | | |
| ACT | TGG | CAA | CCG | ATA | TTT | ACA | AAC | TCA | GAA | GAT | GAA | TTT | TAT | GTG | GAA | | 1848 |
| Thr | Trp | Gln | Pro | Ile | Phe | Thr | Asn | Ser | Glu | Asp | Glu | Phe | Tyr | Val | Glu | | |
| 560 | | | | | 565 | | | | | 570 | | | | | 575 | | |
| GTC | GAG | AGG | CGA | TCC | CTG | CAA | ACA | ACA | AGT | GAT | CAG | CAG | AAC | ATC | AAA | | 1896 |
| Val | Glu | Arg | Arg | Ser | Leu | Gln | Thr | Thr | Ser | Asp | Gln | Gln | Asn | Ile | Lys | | |
| | | | | 580 | | | | | 585 | | | | | 590 | | | |
| GTG | CCT | GGG | AAC | CTG | ACC | TCG | GTG | CTA | CTG | AGC | AAC | TTA | GTC | CCC | AGG | | 1944 |
| Val | Pro | Gly | Asn | Leu | Thr | Ser | Val | Leu | Leu | Ser | Asn | Leu | Val | Pro | Arg | | |
| | | | 595 | | | | | 600 | | | | | 605 | | | | |
| GAG | CAG | TAC | ACA | GTC | CGA | GCT | AGA | GTC | AAC | ACC | AAG | GCG | CAG | GGG | GAG | | 1992 |
| Glu | Gln | Tyr | Thr | Val | Arg | Ala | Arg | Val | Asn | Thr | Lys | Ala | Gln | Gly | Glu | | |
| | | 610 | | | | | 615 | | | | | 620 | | | | | |
| TGG | AGT | GAA | GAA | CTC | AGG | GCC | TGG | ACC | CTT | AGT | GAC | ATT | CTC | CCT | CCT | | 2040 |
| Trp | Ser | Glu | Glu | Leu | Arg | Ala | Trp | Thr | Leu | Ser | Asp | Ile | Leu | Pro | Pro | | |
| | 625 | | | | | 630 | | | | | 635 | | | | | | |
| CAA | CCA | GAA | AAC | ATC | AAG | ATC | TCC | AAC | ATC | ACT | GAC | TCC | ACA | GCT | ATG | | 2088 |
| Gln | Pro | Glu | Asn | Ile | Lys | Ile | Ser | Asn | Ile | Thr | Asp | Ser | Thr | Ala | Met | | |
| 640 | | | | | 645 | | | | | 650 | | | | | 655 | | |
| GTT | TCT | TGG | ACA | ATA | GTG | GAT | GGC | TAT | TCG | ATT | TCT | TCC | ATC | ATC | ATC | | 2136 |
| Val | Ser | Trp | Thr | Ile | Val | Asp | Gly | Tyr | Ser | Ile | Ser | Ser | Ile | Ile | Ile | | |
| | | | | 660 | | | | | 665 | | | | | 670 | | | |
| CGG | TAT | AAG | GTT | CAG | GGC | AAA | AAT | GAA | GAC | CAG | CAC | ATT | GAT | GTG | AAG | | 2184 |
| Arg | Tyr | Lys | Val | Gln | Gly | Lys | Asn | Glu | Asp | Gln | His | Ile | Asp | Val | Lys | | |
| | | | 675 | | | | | 680 | | | | | 685 | | | | |
| ATC | AAG | AAT | GCT | ACC | GTT | ACT | CAG | TAC | CAG | CTC | AAG | GGC | CTA | GAG | CCA | | 2232 |
| Ile | Lys | Asn | Ala | Thr | Val | Thr | Gln | Tyr | Gln | Leu | Lys | Gly | Leu | Glu | Pro | | |
| | | 690 | | | | | 695 | | | | | 700 | | | | | |
| GAG | ACT | ACA | TAC | CAT | GTG | GAT | ATT | TTT | GCT | GAG | AAC | AAC | ATA | GGA | TCA | | 2280 |
| Glu | Thr | Thr | Tyr | His | Val | Asp | Ile | Phe | Ala | Glu | Asn | Asn | Ile | Gly | Ser | | |
| | 705 | | | | | 710 | | | | | 715 | | | | | | |
| AGC | AAC | CCA | GCC | TTT | TCT | CAT | GAA | CTG | AGG | ACG | CTT | CCA | CAT | TCC | CCA | | 2328 |
| Ser | Asn | Pro | Ala | Phe | Ser | His | Glu | Leu | Arg | Thr | Leu | Pro | His | Ser | Pro | | |
| 720 | | | | | 725 | | | | | 730 | | | | | 735 | | |
| GGC | TCT | GCA | GAC | CTC | GGA | GGG | GGA | AAG | ATG | CTA | CTC | ATA | GCC | ATC | CTT | | 2376 |

```
                                            -continued

Gly Ser Ala Asp Leu Gly Gly Gly Lys Met Leu Leu Ile Ala Ile Leu
                740                 745                 750

GGG TCG GCT GGA ATG ACT TGC ATC ACC GTG CTG TTG GCG TTT CTG ATT    2424
Gly Ser Ala Gly Met Thr Cys Ile Thr Val Leu Leu Ala Phe Leu Ile
            755                 760                 765

ATG TTG CAA CTG AAG AGA GCA AAT GTC CAA AGG AGA ATG GCT CAG GCA    2472
Met Leu Gln Leu Lys Arg Ala Asn Val Gln Arg Arg Met Ala Gln Ala
        770                 775                 780

TTC CAG AAC AGA GAA GAA CCA GCT GTG CAG TTT AAC TCA GGA ACT CTG    2520
Phe Gln Asn Arg Glu Glu Pro Ala Val Gln Phe Asn Ser Gly Thr Leu
    785                 790                 795

GCC CTT AAC AGG AAG GCC AAA AAC AAT CCA GAT CCC ACA ATT TAT CCT    2568
Ala Leu Asn Arg Lys Ala Lys Asn Asn Pro Asp Pro Thr Ile Tyr Pro
800                 805                 810                 815

GTG CTT GAC TGG AAT GAC ATC AAG ATC GGA GAG GGC AAC TTT GGC CAG    2616
Val Leu Asp Trp Asn Asp Ile Lys Ile Gly Glu Gly Asn Phe Gly Gln
                820                 825                 830

GTT CTG AAG GCA CGC ATC AAG AAG GAT GGG TTA CGG ATG GAT GCC GCC    2664
Val Leu Lys Ala Arg Ile Lys Lys Asp Gly Leu Arg Met Asp Ala Ala
            835                 840                 845

ATC AAG AGG ATG AAA GAG TAT GCC TCC AAA GAT GAT CAC AGG GAC TTC    2712
Ile Lys Arg Met Lys Glu Tyr Ala Ser Lys Asp Asp His Arg Asp Phe
        850                 855                 860

GCA GGA GAA CTG GAG GTT CTT TGT AAA CTT GGA CAC CAT CCA AAC ATC    2760
Ala Gly Glu Leu Glu Val Leu Cys Lys Leu Gly His His Pro Asn Ile
    865                 870                 875

ATT AAT CTC TTG GGA GCA TGT GAA CAC CGA GGC TAT TTG TAC CTA GCT    2808
Ile Asn Leu Leu Gly Ala Cys Glu His Arg Gly Tyr Leu Tyr Leu Ala
880                 885                 890                 895

ATT GAG TAT GCC CCG CAT GGA AAC CTC CTG GAC TTC CTG CGT AAG AGC    2856
Ile Glu Tyr Ala Pro His Gly Asn Leu Leu Asp Phe Leu Arg Lys Ser
                900                 905                 910

AGA GTG CTA GAG ACA GAC CCT GCT TTT GCC ATC GCC AAC AGT ACA GCT    2904
Arg Val Leu Glu Thr Asp Pro Ala Phe Ala Ile Ala Asn Ser Thr Ala
            915                 920                 925

TCC ACA CTG TCC TCC CAA CAG CTT CTT CAT TTT GCT GCA GAT GTG GCC    2952
Ser Thr Leu Ser Ser Gln Gln Leu Leu His Phe Ala Ala Asp Val Ala
        930                 935                 940

CGG GGG ATG GAC TAC TTG AGC CAG AAA CAG TTT ATC CAC AGG GAC CTG    3000
Arg Gly Met Asp Tyr Leu Ser Gln Lys Gln Phe Ile His Arg Asp Leu
    945                 950                 955

GCT GCC AGA AAC ATT TTA GTT GGT GAA AAC TAC ATA GCC AAA ATA GCA    3048
Ala Ala Arg Asn Ile Leu Val Gly Glu Asn Tyr Ile Ala Lys Ile Ala
960                 965                 970                 975

GAT TTT GGA TTG TCA CGA GGT CAA GAA GTG TAT GTG AAA AAG ACA ATG    3096
Asp Phe Gly Leu Ser Arg Gly Gln Glu Val Tyr Val Lys Lys Thr Met
                980                 985                 990

GGA AGG CTC CCA GTG CGT TGG ATG GCA ATC GAA TCA CTG AAC TAT AGT    3144
Gly Arg Leu Pro Val Arg Trp Met Ala Ile Glu Ser Leu Asn Tyr Ser
            995                 1000                1005

GTC TAT ACA ACC AAC AGT GAT GTC TGG TCC TAT GGT GTA TTG CTC TGG    3192
Val Tyr Thr Thr Asn Ser Asp Val Trp Ser Tyr Gly Val Leu Leu Trp
        1010                1015                1020

GAG ATT GTT AGC TTA GGA GGC ACC CCC TAC TGC GGC ATG ACG TGC GCG    3240
Glu Ile Val Ser Leu Gly Gly Thr Pro Tyr Cys Gly Met Thr Cys Ala
    1025                1030                1035

GAG CTC TAT GAG AAG CTA CCC CAG GGC TAC AGG CTG GAG AAG CCC CTG    3288
Glu Leu Tyr Glu Lys Leu Pro Gln Gly Tyr Arg Leu Glu Lys Pro Leu
1040                1045                1050                1055
```

| | | | | | | | | | | | | | | | | |
|---|---|---|---|---|---|---|---|---|---|---|---|---|---|---|---|---|
|AAC|TGT|GAT|GAT|GAG|GTG|TAT|GAT|CTA|ATG|AGA|CAG|TGC|TGG|AGG|GAG|3336|
|Asn|Cys|Asp|Asp|Glu|Val|Tyr|Asp|Leu|Met|Arg|Gln|Cys|Trp|Arg|Glu| |
| | | |1060| | | | |1065| | | |1070| | | | |
|AAG|CCT|TAT|GAG|AGA|CCA|TCA|TTT|GCC|CAG|ATA|TTG|GTG|TCC|TTA|AAC|3384|
|Lys|Pro|Tyr|Glu|Arg|Pro|Ser|Phe|Ala|Gln|Ile|Leu|Val|Ser|Leu|Asn| |
| | |1075| | | | |1080| | | | |1085| | | | |
|AGG|ATG|CTG|GAA|GAA|CGG|AAG|ACA|TAC|GTG|AAC|ACC|ACA|CTG|TAT|GAG|3432|
|Arg|Met|Leu|Glu|Glu|Arg|Lys|Thr|Tyr|Val|Asn|Thr|Thr|Leu|Tyr|Glu| |
| | |1090| | | | |1095| | | | |1100| | | | |
|AAG|TTT|ACC|TAT|GCA|GGA|ATT|GAC|TGC|TCT|GCG|GAA|GAA|GCA|GCC| |3477|
|Lys|Phe|Thr|Tyr|Ala|Gly|Ile|Asp|Cys|Ser|Ala|Glu|Glu|Ala|Ala| | |
| | |1105| | | | |1110| | | | |1115| | | | |

```
TAGAGCAGAA CTCTTCATGT ACAACGGCCA TTTCTCCTCA CTGGCGCGAG AGCCTTGACA       3537
CCTGTACCAA GCAAGCCACC CACTGCCAAG AGATGTGATA TATAAGTGTA TATATTGTGC       3597
TGTGTTTGGG ACCCTCCTCA TACAGCTCGT GCGGATCTGC AGTGTGTTCT GACTCTAATG       3657
TGACTGTATA TACTGCTCGG AGTAAGAATG TGCTAAGATC AGAATGCCTG TTCGTGGTTT       3717
CATATAATAT ATTTTTCTAA AAGCATAGAT TGCACAGGAA GGTATGAGTA CAAATACTGT       3777
AATGCATAAC TTGTTATTGT CCTAGATGTG TTTGACATTT TTCCTTTACA ACTGAATGCT       3837
ATAAAAGTGT TTTGCTGTGT GCGCGTAAGA TACTGTTCGT TAAAATAAGC ATTCCCTTGA       3897
CAGCACAGGA AGAAAGCGA  GGGAAATGTA TGGATTATAT TAAATGTGGG TTACTACACA       3957
AGAGGCCGAA CATTCCAAGT AGCAGAAGAG AGGGTCTCTC AACTCTGCTC CTCACCTGCA       4017
GAAGCCAGTT TGTTTGGCCA TGTGACAATT GTCCTGTGTT TTTATAGCAC CCAAATCATT       4077
CTAAAATATG AACATCTAAA AACTTTGCTA GGAGACTAAG AACCTTTGGA GAGATAGATA       4137
TAAGTACGGT CAAAAAACAA AACTGCGCCA TGGTACCC                               4175
```

( 2 ) INFORMATION FOR SEQ ID NO:2:

( i ) SEQUENCE CHARACTERISTICS:
    ( A ) LENGTH: 1118 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Asp Ser Leu Ala Gly Leu Val Leu Cys Gly Val Ser Leu Leu Leu
 1               5                  10                  15

Tyr Gly Val Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp His Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Gln Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Arg Gly Asp Asn Val Asn Ile Ser Phe Lys
    130                 135                 140
```

-continued

| | | | | | | | | | | | | | | |
|---|---|---|---|---|---|---|---|---|---|---|---|---|---|---|
| Lys 145 | Val | Leu | Ile | Lys 150 | Glu | Asp | Ala | Val 155 | Ile | Tyr | Lys | Asn | Gly | Ser 160 |
| Phe | Ile | His | Ser | Val 165 | Pro | Arg | His | Glu 170 | Val | Pro | Asp | Ile | Leu | Glu 175 | Val |
| His | Leu | Pro | His 180 | Ala | Gln | Pro | Gln | Asp 185 | Ala | Gly | Val | Tyr | Ser 190 | Ala | Arg |
| Tyr | Ile | Gly 195 | Gly | Asn | Leu | Phe | Thr 200 | Ser | Ala | Phe | Thr | Arg 205 | Leu | Ile | Val |
| Arg | Arg 210 | Cys | Glu | Ala | Gln | Lys 215 | Trp | Gly | Pro | Asp | Cys 220 | Ser | Arg | Pro | Cys |
| Thr 225 | Thr | Cys | Lys | Asn | Asn 230 | Gly | Val | Cys | His | Glu 235 | Asp | Thr | Gly | Glu | Cys 240 |
| Ile | Cys | Pro | Pro | Gly 245 | Phe | Met | Gly | Arg | Thr 250 | Cys | Glu | Lys | Ala | Cys 255 | Glu |
| Pro | His | Thr | Phe 260 | Gly | Arg | Thr | Cys | Lys 265 | Glu | Arg | Cys | Ser | Gly 270 | Pro | Glu |
| Gly | Cys | Lys 275 | Ser | Tyr | Val | Phe | Cys 280 | Leu | Pro | Asp | Pro | Tyr 285 | Gly | Cys | Ser |
| Cys | Ala 290 | Thr | Gly | Trp | Arg | Gly 295 | Leu | Gln | Cys | Asn | Glu 300 | Ala | Cys | Pro | Ser |
| Gly 305 | Tyr | Tyr | Gly | Pro | Asp 310 | Cys | Lys | Leu | Arg | Cys 315 | His | Cys | Thr | Asn | Glu 320 |
| Glu | Ile | Cys | Asp | Arg 325 | Phe | Gln | Gly | Cys | Leu 330 | Cys | Ser | Gln | Gly | Trp 335 | Gln |
| Gly | Leu | Gln | Cys 340 | Glu | Lys | Glu | Gly | Arg 345 | Pro | Arg | Met | Thr | Pro 350 | Gln | Ile |
| Glu | Asp | Leu 355 | Pro | Asp | His | Ile | Glu 360 | Val | Asn | Ser | Gly | Lys 365 | Phe | Asn | Pro |
| Ile | Cys 370 | Lys | Ala | Ser | Gly | Trp 375 | Pro | Leu | Pro | Thr | Ser 380 | Glu | Glu | Met | Thr |
| Leu 385 | Val | Lys | Pro | Asp | Gly 390 | Thr | Val | Leu | Gln | Pro 395 | Asn | Asp | Phe | Asn | Tyr 400 |
| Thr | Asp | Arg | Phe | Ser 405 | Val | Ala | Ile | Phe | Thr 410 | Val | Asn | Arg | Val | Leu 415 | Pro |
| Pro | Asp | Ser | Gly 420 | Val | Trp | Val | Cys | Ser 425 | Val | Asn | Thr | Val | Ala 430 | Gly | Met |
| Val | Glu | Lys 435 | Pro | Phe | Asn | Ile | Ser 440 | Val | Lys | Val | Leu | Pro 445 | Glu | Pro | Leu |
| His | Ala 450 | Pro | Asn | Val | Ile | Asp 455 | Thr | Gly | His | Asn | Phe 460 | Ala | Ile | Ile | Asn |
| Ile 465 | Ser | Ser | Glu | Pro | Tyr 470 | Phe | Gly | Asp | Gly | Pro 475 | Ile | Lys | Ser | Lys | Lys 480 |
| Leu | Phe | Tyr | Lys | Pro 485 | Val | Asn | Gln | Ala | Trp 490 | Lys | Tyr | Ile | Glu | Val 495 | Thr |
| Asn | Glu | Ile | Phe 500 | Thr | Leu | Asn | Tyr | Leu 505 | Glu | Pro | Arg | Thr | Asp 510 | Tyr | Glu |
| Leu | Cys | Val 515 | Gln | Leu | Ala | Arg | Pro 520 | Gly | Glu | Gly | Gly | Glu 525 | Gly | His | Pro |
| Gly | Pro 530 | Val | Arg | Arg | Phe | Thr 535 | Thr | Ala | Cys | Ile | Gly 540 | Leu | Pro | Pro | Pro |
| Arg 545 | Gly | Leu | Ser | Leu | Leu 550 | Pro | Lys | Ser | Gln | Thr 555 | Ala | Leu | Asn | Leu | Thr 560 |
| Trp | Gln | Pro | Ile | Phe | Thr | Asn | Ser | Glu | Asp | Glu | Phe | Tyr | Val | Glu | Val |

|  |  | 565 |  |  |  |  | 570 |  |  |  |  | 575 |  |
|---|---|---|---|---|---|---|---|---|---|---|---|---|---|

Glu Arg Arg Ser Leu Gln Thr Thr Ser Asp Gln Gln Asn Ile Lys Val
            580                 585              590

Pro Gly Asn Leu Thr Ser Val Leu Leu Ser Asn Leu Val Pro Arg Glu
            595              600              605

Gln Tyr Thr Val Arg Ala Arg Val Asn Thr Lys Ala Gln Gly Glu Trp
            610              615              620

Ser Glu Glu Leu Arg Ala Trp Thr Leu Ser Asp Ile Leu Pro Pro Gln
625              630              635              640

Pro Glu Asn Ile Lys Ile Ser Asn Ile Thr Asp Ser Thr Ala Met Val
                645              650              655

Ser Trp Thr Ile Val Asp Gly Tyr Ser Ile Ser Ser Ile Ile Ile Arg
            660              665              670

Tyr Lys Val Gln Gly Lys Asn Glu Asp Gln His Ile Asp Val Lys Ile
            675              680              685

Lys Asn Ala Thr Val Thr Gln Tyr Gln Leu Lys Gly Leu Glu Pro Glu
            690              695              700

Thr Thr Tyr His Val Asp Ile Phe Ala Glu Asn Asn Ile Gly Ser Ser
705              710              715              720

Asn Pro Ala Phe Ser His Glu Leu Arg Thr Leu Pro His Ser Pro Gly
                725              730              735

Ser Ala Asp Leu Gly Gly Gly Lys Met Leu Leu Ile Ala Ile Leu Gly
            740              745              750

Ser Ala Gly Met Thr Cys Ile Thr Val Leu Leu Ala Phe Leu Ile Met
            755              760              765

Leu Gln Leu Lys Arg Ala Asn Val Gln Arg Arg Met Ala Gln Ala Phe
770              775              780

Gln Asn Arg Glu Glu Pro Ala Val Gln Phe Asn Ser Gly Thr Leu Ala
785              790              795              800

Leu Asn Arg Lys Ala Lys Asn Asn Pro Asp Pro Thr Ile Tyr Pro Val
            805              810              815

Leu Asp Trp Asn Asp Ile Lys Ile Gly Glu Gly Asn Phe Gly Gln Val
            820              825              830

Leu Lys Ala Arg Ile Lys Lys Asp Gly Leu Arg Met Asp Ala Ala Ile
            835              840              845

Lys Arg Met Lys Glu Tyr Ala Ser Lys Asp Asp His Arg Asp Phe Ala
850              855              860

Gly Glu Leu Glu Val Leu Cys Lys Leu Gly His His Pro Asn Ile Ile
865              870              875              880

Asn Leu Leu Gly Ala Cys Glu His Arg Gly Tyr Leu Tyr Leu Ala Ile
            885              890              895

Glu Tyr Ala Pro His Gly Asn Leu Leu Asp Phe Leu Arg Lys Ser Arg
            900              905              910

Val Leu Glu Thr Asp Pro Ala Phe Ala Ile Ala Asn Ser Thr Ala Ser
            915              920              925

Thr Leu Ser Ser Gln Gln Leu Leu His Phe Ala Ala Asp Val Ala Arg
930              935              940

Gly Met Asp Tyr Leu Ser Gln Lys Gln Phe Ile His Arg Asp Leu Ala
945              950              955              960

Ala Arg Asn Ile Leu Val Gly Glu Asn Tyr Ile Ala Lys Ile Ala Asp
            965              970              975

Phe Gly Leu Ser Arg Gly Gln Glu Val Tyr Val Lys Lys Thr Met Gly
            980              985              990

```
Arg  Leu  Pro  Val  Arg  Trp  Met  Ala  Ile  Glu  Ser  Leu  Asn  Tyr  Ser  Val
          995                 1000                     1005

Tyr  Thr  Thr  Asn  Ser  Asp  Val  Trp  Ser  Tyr  Gly  Val  Leu  Leu  Trp  Glu
     1010                     1015                     1020

Ile  Val  Ser  Leu  Gly  Gly  Thr  Pro  Tyr  Cys  Gly  Met  Thr  Cys  Ala  Glu
1025                1030                     1035                          1040

Leu  Tyr  Glu  Lys  Leu  Pro  Gln  Gly  Tyr  Arg  Leu  Glu  Lys  Pro  Leu  Asn
               1045                     1050                     1055

Cys  Asp  Asp  Glu  Val  Tyr  Asp  Leu  Met  Arg  Gln  Cys  Trp  Arg  Glu  Lys
               1060                     1065                     1070

Pro  Tyr  Glu  Arg  Pro  Ser  Phe  Ala  Gln  Ile  Leu  Val  Ser  Leu  Asn  Arg
          1075                     1080                     1085

Met  Leu  Glu  Glu  Arg  Lys  Thr  Tyr  Val  Asn  Thr  Thr  Leu  Tyr  Glu  Lys
          1090                     1095                     1100

Phe  Thr  Tyr  Ala  Gly  Ile  Asp  Cys  Ser  Ala  Glu  Glu  Ala  Ala
1105                     1110                     1115
```

( 2 ) INFORMATION FOR SEQ ID NO:3:

( i ) SEQUENCE CHARACTERISTICS:
            ( A ) LENGTH: 1601 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Mus pahari
            ( D ) DEVELOPMENTAL STAGE: Embryo ( v i i ) IMMEDIATE SOURCE:
            ( A ) LIBRARY: murine embryonic lambda gt10 cDNA library
            ( B ) CLONE: 1.6kb clone ( v i i i ) POSITION IN GENOME:
            ( A ) CHROMOSOME/SEGMENT: 4
            ( B ) MAP POSITION: Between the brown and pmv-23 loci ( i x ) FEATURE:
            ( A ) NAME/KEY: CDS
            ( B ) LOCATION: 1..903

( x i ) SEQUENCE DESCRIPTION: SEQ ID NO:3:

```
ATC  AAG  TTT  CAA  GAC  GTG  ATC  GGA  GAG  GGC  AAC  TTT  GGC  CAG  GTT  CTG       48
Ile  Lys  Phe  Gln  Asp  Val  Ile  Gly  Glu  Gly  Asn  Phe  Gly  Gln  Val  Leu
 1             5                    10                     15

AAG  GCA  CGC  ATC  AAG  AAG  GAT  GGG  TTA  CGG  ATG  GAT  GCC  GCC  ATC  AAG       96
Lys  Ala  Arg  Ile  Lys  Lys  Asp  Gly  Leu  Arg  Met  Asp  Ala  Ala  Ile  Lys
               20                  25                          30

AGG  ATG  AAA  GAG  TAT  GCC  TCC  AAA  GAT  GAT  CAC  AGG  GAC  TTC  GCA  GGA      144
Arg  Met  Lys  Glu  Tyr  Ala  Ser  Lys  Asp  Asp  His  Arg  Asp  Phe  Ala  Gly
          35                       40                      45

GAA  CTG  GAG  GTT  CTT  TGT  AAA  CTT  GGA  CAC  CAT  CCA  AAC  ATC  ATT  AAT      192
Glu  Leu  Glu  Val  Leu  Cys  Lys  Leu  Gly  His  His  Pro  Asn  Ile  Ile  Asn
     50                  55                      60

CTC  TTG  GGA  GCA  TGT  GAA  CAC  CGA  GGC  TAT  TTG  TAC  CTA  GCT  ATT  GAG      240
Leu  Leu  Gly  Ala  Cys  Glu  His  Arg  Gly  Tyr  Leu  Tyr  Leu  Ala  Ile  Glu
65                        70                     75                          80

TAT  GCC  CCG  CAT  GGA  AAC  CTC  CTG  GAC  TTC  CTG  CGT  AAG  AGC  AGA  GTG      288
Tyr  Ala  Pro  His  Gly  Asn  Leu  Leu  Asp  Phe  Leu  Arg  Lys  Ser  Arg  Val
               85                       90                      95

CTA  GAG  ACA  GAC  CCT  GCT  TTT  GCC  ATC  GCC  AAC  AGT  ACA  GCT  TCC  ACA      336
```

```
Leu Glu Thr Asp Pro Ala Phe Ala Ile Ala Asn Ser Thr Ala Ser Thr
            100                 105                 110

CTG TCC TCC CAA CAG CTT CTT CAT TTT GCT GCA GAT GTG GCC CGG GGG         384
Leu Ser Ser Gln Gln Leu Leu His Phe Ala Ala Asp Val Ala Arg Gly
        115                 120                 125

ATG GAC TAC TTG AGC CAG AAA CAG TTT ATC CAC AGG GAC CTG GCT GCC         432
Met Asp Tyr Leu Ser Gln Lys Gln Phe Ile His Arg Asp Leu Ala Ala
130                 135                 140

AGA AAC ATT TTA GTT GGT GAA AAC TAC ATA GCC AAA ATA GCA GAT TTT         480
Arg Asn Ile Leu Val Gly Glu Asn Tyr Ile Ala Lys Ile Ala Asp Phe
145                 150                 155                 160

GGA TTG TCA CGA GGT CAA GAA GTG TAT GTG AAA AAG ACA ATG GGA AGG         528
Gly Leu Ser Arg Gly Gln Glu Val Tyr Val Lys Lys Thr Met Gly Arg
                165                 170                 175

CTC CCA GTG CGT TGG ATG GCA ATC GAA TCA CTG AAC TAT AGT GTC TAT         576
Leu Pro Val Arg Trp Met Ala Ile Glu Ser Leu Asn Tyr Ser Val Tyr
            180                 185                 190

ACA ACC AAC AGT GAT GTC TGG TCC TAT GGT GTA TTG CTC TGG GAG ATT         624
Thr Thr Asn Ser Asp Val Trp Ser Tyr Gly Val Leu Leu Trp Glu Ile
        195                 200                 205

GTT AGC TTA GGA GGC ACC CCC TAC TGC GGC ATG ACG TGC GCG GAG CTC         672
Val Ser Leu Gly Gly Thr Pro Tyr Cys Gly Met Thr Cys Ala Glu Leu
210                 215                 220

TAT GAG AAG CTA CCC CAG GGC TAC AGG CTG GAG AAG CCC CTG AAC TGT         720
Tyr Glu Lys Leu Pro Gln Gly Tyr Arg Leu Glu Lys Pro Leu Asn Cys
225                 230                 235                 240

GAT GAT GAG GTG TAT GAT CTA ATG AGA CAG TGC TGG AGG GAG AAG CCT         768
Asp Asp Glu Val Tyr Asp Leu Met Arg Gln Cys Trp Arg Glu Lys Pro
                245                 250                 255

TAT GAG AGA CCA TCA TTT GCC CAG ATA TTG GTG TCC TTA AAC AGG ATG         816
Tyr Glu Arg Pro Ser Phe Ala Gln Ile Leu Val Ser Leu Asn Arg Met
            260                 265                 270

CTG GAA GAA CGG AAG ACA TAC GTG AAC ACC ACA CTG TAT GAG AAG TTT         864
Leu Glu Glu Arg Lys Thr Tyr Val Asn Thr Thr Leu Tyr Glu Lys Phe
        275                 280                 285

ACC TAT GCA GGA ATT GAC TGC TCT GCG GAA GAA GCA GCC TAGAGCAGAA          913
Thr Tyr Ala Gly Ile Asp Cys Ser Ala Glu Glu Ala Ala
290                 295                 300

CTCTTCATGT ACAACGGCCA TTTCTCCTCA CTGGCGCGAG AGCCTTGACA CCTGTACCAA       973
GCAAGCCACC CACTGCCAAG AGATGTGATA TATAAGTGTA TATATTGTGC TGTGTTTGGG      1033
ACCCTCCTCA TACAGCTCGT GCGGATCTGC AGTGTGTTCT GACTCTAATG TGACTGTATA      1093
TACTGCTCGG AGTAAGAATG TGCTAAGATC AGAATGCCTG TTCGTGGTTT CATATAATAT      1153
ATTTTTCTAA AAGCATAGAT TGCACAGGAA GGTATGAGTA CAAATACTGT AATGCATAAC      1213
TTGTTATTGT CCTAGATGTG TTTGACATTT TTCCTTTACA ACTGAATGCT ATAAAAGTGT      1273
TTTGCTGTGT GCGCGTAAGA TACTGTTCGT TAAAATAAGC ATTCCCTTGA CAGCACAGGA      1333
AGAAAAGCGA GGGAAATGTA TGGATTATAT TAAATGTGGG TTACTACACA AGAGGCCGAA      1393
CATTCCAAGT AGCAGAAGAG AGGGTCTCTC AACTCTGCTC CTCACCTGCA GAAGCCAGTT      1453
TGTTTGGCCA TGTGACAATT GTCCTGTGTT TTTATAGCAC CCAAATCATT CTAAAATATG      1513
AACATCTAAA AACTTTGCTA GGAGACTAAG AACCTTTGGA GAGATAGATA TAAGTACGGT      1573
CAAAAAACAA AACTGCGCCA TGGTACCC                                        1601
```

( 2 ) INFORMATION FOR SEQ ID NO:4:

( i ) SEQUENCE CHARACTERISTICS:

(A) LENGTH: 301 amino acids
(B) TYPE: amino acid
(D) TOPOLOGY: linear (ii) MOLECULE TYPE: protein (xi) SEQUENCE DESCRIPTION: SEQ ID NO:4:

| Ile | Lys | Phe | Gln | Asp | Val | Ile | Gly | Glu | Gly | Asn | Phe | Gly | Gln | Val | Leu |
|---|---|---|---|---|---|---|---|---|---|---|---|---|---|---|---|
| 1 | | | | 5 | | | | | 10 | | | | | 15 | |
| Lys | Ala | Arg | Ile | Lys | Lys | Asp | Gly | Leu | Arg | Met | Asp | Ala | Ala | Ile | Lys |
| | | | 20 | | | | | 25 | | | | | 30 | | |
| Arg | Met | Lys | Glu | Tyr | Ala | Ser | Lys | Asp | Asp | His | Arg | Asp | Phe | Ala | Gly |
| | | 35 | | | | | 40 | | | | | 45 | | | |
| Glu | Leu | Glu | Val | Leu | Cys | Lys | Leu | Gly | His | His | Pro | Asn | Ile | Ile | Asn |
| | 50 | | | | | 55 | | | | | 60 | | | | |
| Leu | Leu | Gly | Ala | Cys | Glu | His | Arg | Gly | Tyr | Leu | Tyr | Leu | Ala | Ile | Glu |
| 65 | | | | | 70 | | | | | 75 | | | | | 80 |
| Tyr | Ala | Pro | His | Gly | Asn | Leu | Leu | Asp | Phe | Leu | Arg | Lys | Ser | Arg | Val |
| | | | | 85 | | | | | 90 | | | | | 95 | |
| Leu | Glu | Thr | Asp | Pro | Ala | Phe | Ala | Ile | Ala | Asn | Ser | Thr | Ala | Ser | Thr |
| | | | 100 | | | | | 105 | | | | | 110 | | |
| Leu | Ser | Ser | Gln | Gln | Leu | Leu | His | Phe | Ala | Ala | Asp | Val | Ala | Arg | Gly |
| | | 115 | | | | | 120 | | | | | 125 | | | |
| Met | Asp | Tyr | Leu | Ser | Gln | Lys | Gln | Phe | Ile | His | Arg | Asp | Leu | Ala | Ala |
| | 130 | | | | | 135 | | | | | 140 | | | | |
| Arg | Asn | Ile | Leu | Val | Gly | Glu | Asn | Tyr | Ile | Ala | Lys | Ile | Ala | Asp | Phe |
| 145 | | | | | 150 | | | | | 155 | | | | | 160 |
| Gly | Leu | Ser | Arg | Gly | Gln | Glu | Val | Tyr | Val | Lys | Lys | Thr | Met | Gly | Arg |
| | | | | 165 | | | | | 170 | | | | | 175 | |
| Leu | Pro | Val | Arg | Trp | Met | Ala | Ile | Glu | Ser | Leu | Asn | Tyr | Ser | Val | Tyr |
| | | | 180 | | | | | 185 | | | | | 190 | | |
| Thr | Thr | Asn | Ser | Asp | Val | Trp | Ser | Tyr | Gly | Val | Leu | Leu | Trp | Glu | Ile |
| | | 195 | | | | | 200 | | | | | 205 | | | |
| Val | Ser | Leu | Gly | Gly | Thr | Pro | Tyr | Cys | Gly | Met | Thr | Cys | Ala | Glu | Leu |
| 210 | | | | | 215 | | | | | 220 | | | | | |
| Tyr | Glu | Lys | Leu | Pro | Gln | Gly | Tyr | Arg | Leu | Glu | Lys | Pro | Leu | Asn | Cys |
| 225 | | | | | 230 | | | | | 235 | | | | | 240 |
| Asp | Asp | Glu | Val | Tyr | Asp | Leu | Met | Arg | Gln | Cys | Trp | Arg | Glu | Lys | Pro |
| | | | | 245 | | | | | 250 | | | | | 255 | |
| Tyr | Glu | Arg | Pro | Ser | Phe | Ala | Gln | Ile | Leu | Val | Ser | Leu | Asn | Arg | Met |
| | | | 260 | | | | | 265 | | | | | 270 | | |
| Leu | Glu | Glu | Arg | Lys | Thr | Tyr | Val | Asn | Thr | Thr | Leu | Tyr | Glu | Lys | Phe |
| | | 275 | | | | | 280 | | | | | 285 | | | |
| Thr | Tyr | Ala | Gly | Ile | Asp | Cys | Ser | Ala | Glu | Glu | Ala | Ala | | | |
| | 290 | | | | | 295 | | | | | 300 | | | | |

(2) INFORMATION FOR SEQ ID NO:5:

(i) SEQUENCE CHARACTERISTICS:
(A) LENGTH: 847 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Mus pahari (vii) IMMEDIATE SOURCE:
    (A) LIBRARY: mouse genomic bacteriophage library (viii) POSITION IN GENOME:
    (A) CHROMOSOME/SEGMENT: 4
    (B) MAP POSITION: Between the brown and pmv-23 loci (xi) SEQUENCE DESCRIPTION: SEQ ID NO:5:

| | | | | | | |
|---|---|---|---|---|---|---|
| GCAAGTGCTG | CTCCCCGTGC | CCCAAAGCCC | CTTCTGTCAG | GGATCCCAAA | TGCACCCAG | 60 |
| AGAACAGCTT | AGCCTGCAAG | GGCTGGTCCT | CATCGCATAC | CATACATAGT | GGAGGCTTGT | 120 |
| TATTCAATTC | CTGGCCTATG | AGAGGATACC | CCTATTGTTC | CTGAAAATGC | TGACCAGGAC | 180 |
| CTTACTTGTA | ACAAGATCC | CTCTGCCCCA | CAATCCAGTT | AAGGCAGGAG | CAGGACCGGA | 240 |
| GCAGGAGCAG | AAGATAAGCC | TTGGATGAAG | GGCAAGATGG | ATAGGGCTCG | CTCTGCCCCA | 300 |
| AGCCCTGCTG | ATACCAAGTG | CCTTTAAGAT | ACAGCCTTTC | CCATCCTAAT | CTGCAAAGGA | 360 |
| AACAGGAAAA | AGGAACTTAA | CCCTCCCTGT | GCTCAGACAG | AAATGAGACT | GTTACCGCCT | 420 |
| GCTTCTGTGG | TGTTTCTCCT | TGCCGCCAAC | TTGTAAACAA | GAGCGAGTGG | ACCATGAGAG | 480 |
| CGGGAAGTCG | CAAAGTTGTG | AGTTGTTGAA | AGCTTCCCAG | GGACTCATGC | TCATCTGTGG | 540 |
| ACGCTGGATG | GGGAGATCTG | GGGAAGTATG | GACTCTTTAG | CCGGCTTAGT | TCTCTGTGGA | 600 |
| GTCAGCTTGC | TCCTTTATGG | TAAGTTTTGG | CTTGATGTTT | ATTTGTGTGT | GTGTGTCATG | 660 |
| TTTTAACAAC | AGTGACTTCT | CGCCATTCTC | TCTCTCACCA | AACCTTCGAT | TTGGTGACCC | 720 |
| TGACACTGCT | TTTCTGAGAC | TCTCCAGTTT | ACACATGGCA | ACGGTTTTGA | AGTTCAGATT | 780 |
| CCAGCGGCAC | CAGCTGGTTT | TCAGCCATCT | TCTTGTAGAC | AGATGCTGCC | TTCCTGGGTT | 840 |
| GCCACGG | | | | | | 847 |

We claim

1. An isolated transcriptional regulatory element comprising (a) a nucleotide sequence having nucleotides 1 to 560 of the sequence as shown in SEQ. ID. NO. 5, and (b) nucleotide sequences complementary to (a).

2. A recombinant DNA molecule comprising a transcriptional regulatory element as claimed in claim 1 and a gene operatively linked thereto.

3. A recombinant DNA molecule as claimed in claim 2 wherein the gene is a reporter gene.

4. A recombinant DNA molecule as claimed in claim 2 wherein the gene encodes a toxic or therapeutic substance or an angiogenic factor.

5. A recombinant DNA molecule comprising a transcriptional regulatory element as claimed in claim 1 operatively linked to a gene and a reporter gene.

6. A recombinant DNA molecule as claimed in claim 5 wherein the reporter gene is a lacZ gene which codes for β-galactosidase, a neo gene which codes for neomycin phosphotransferase, a cat gene which codes for chloramphenicol acetyltransferase, a dhfr gene which codes for dihydrofolate reductase, a aphIV gene which codes for hygromycin phosphotransferase, a lux gene which codes for luciferase, or a uidA gene which codes for β-glucuronidase.

7. A recombinant DNA molecule comprising a transcriptional regulatory element as claimed in claim 1 operatively linked to a gene encoding a toxic or therapeutic substance or an angiogenic factor, and a reporter gene.

8. A cell line comprising transformant animal host cells including a recombinant DNA molecule as claimed in claim 2, 3, 4, 5, 7 or 6.

9. A cell line comprising transformant mouse endothelial host cells including a recombinant DNA molecule as claimed in claim 2, 3, 4, 5, 7 or 6.

10. A cell line comprising transformant human endothelial host cells including a recombinant DNA molecule as claimed in claim 2, 3, 4, 5, 6 or 7.

* * * * *